(12) United States Patent
Banno et al.

(10) Patent No.: US 7,347,954 B2
(45) Date of Patent: Mar. 25, 2008

(54) COMPOSITION FOR POLYELECTROLYTES, POLYELECTROLYTES, ELECTRICAL DOUBLE LAYER CAPACITORS AND NONAQUEOUS ELECTROLYTE SECONDARY CELLS

(75) Inventors: Kimiyo Banno, Chiba (JP); Kanako Yuyama, Chiba (JP); Kentaro Takagi, Chiba (JP); Gen Masuda, Chiba (JP); Takaya Sato, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 400 days.

(21) Appl. No.: 10/528,051

(22) PCT Filed: Sep. 19, 2003

(86) PCT No.: PCT/JP03/11979
§ 371 (c)(1), (2), (4) Date: Mar. 17, 2005

(87) PCT Pub. No.: WO2004/027789
PCT Pub. Date: Apr. 1, 2004

(65) Prior Publication Data
US 2006/0120021 A1    Jun. 8, 2006

(30) Foreign Application Priority Data
Sep. 20, 2002 (JP) ............................. 2002-274335
Apr. 16, 2003 (JP) ............................. 2003-111763

(51) Int. Cl.
- H01B 1/06 (2006.01)
- H01M 10/40 (2006.01)
- H01G 9/058 (2006.01)
- H01G 9/038 (2006.01)
- C08L 33/14 (2006.01)
- C07C 217/08 (2006.01)
- C07C 311/48 (2006.01)
- C07C 219/06 (2006.01)

(52) U.S. Cl. .................. 252/62.2; 429/314; 429/309; 429/189; 361/502; 361/523; 361/527

(58) Field of Classification Search ............... 252/62.2; 429/314, 309, 189; 361/502, 523, 527
See application file for complete search history.

(56) References Cited

U.S. PATENT DOCUMENTS 4,482,713 A    11/1984  Strickler
5,378,381 A *  1/1995  Takahashi et al. .......... 252/62.2
5,643,490 A *  7/1997  Takahashi et al. .......... 252/62.2
7,154,737 B2   12/2006  Maruo et al.
7,167,353 B2   1/2007   Yuyama et al.

FOREIGN PATENT DOCUMENTS

| JP | 61-152757 A | 7/1986 |
|---|---|---|
| JP | 04-349365 A | 12/1992 |
| JP | 7-118480 A | 5/1995 |
| JP | 07-161588 A | 6/1995 |
| JP | 8-245828 A | 9/1996 |
| JP | 10-83821 A | 3/1998 |
| JP | 11-224831 A | 8/1999 |
| JP | 11-260400 A | 9/1999 |
| JP | 11-307121 A | 11/1999 |
| JP | 2002-3478 A | 1/2002 |
| JP | 2002-251917 A | 9/2002 |
| JP | 2003-86470 A | 3/2003 |
| WO | WO-02/067272 A1 | 8/2002 |

OTHER PUBLICATIONS

Matsumoto et al., "Improvement of ionic conductivity of room temperature molten salt based on quaternary ammonium cation and imide anion," Electrochemical Society Proceedings, vol. 99-41, pp. 186-192, 2000.

(Continued)

Primary Examiner—C. Melissa Koslow
(74) Attorney, Agent, or Firm—Birch, Stewart, Kolasch & Birch, LLP

(57) ABSTRACT

A polymer electrolyte-forming composition containing (A) a quaternary ammonium salt of general formula (1) below and (B) an ionic liquid can be converted into a polymer without compromising the excellent properties of the ionic liquid, thus enabling an electrolyte having an excellent safety and electrical conductivity and also a broad potential window to be obtained.

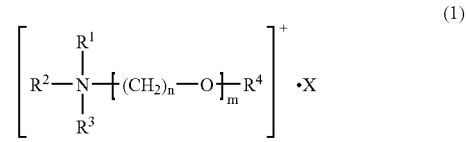

(1)

In formula (1), $R^1$ to $R^3$ are each independently an alkyl group of 1 to 5 carbons or a substituent having a reactive unsaturated bond and any two from among $R^1$ to $R^3$ may together form a ring, and $R^4$ is methyl, ethyl or a substituent having a reactive unsaturated bond, with the proviso that at least one of $R^1$ to $R^4$ is a substituent having a reactive unsaturated bond. X is a monovalent anion, the letter m is an integer from 1 to 8, and the letter n is an integer from 1 to 4.

15 Claims, No Drawings

OTHER PUBLICATIONS

Rios et al., "Generation and study of the reactivity of α-ammonium distonic radical cations in solution," Journal of American Chemical Society, vol. 118, No. 45, pp. 11313-11314, 1996.

Stuff et al., "A new room-temperature molten salt electrolyte," Journal of the Electrochemical Society, vol. 137, No. 5, pp. 1492-1493, 1990.

Cooper et al., "Versatile organic iodide melts and glasses with high mole fractions of lithium iodide: glass transition temperatures and electrical conductivities," Solid State Ionics, vol. 9 and 10, pp. 617-622, 1983.

A.B. McEwen et al., "Electrochemical Properties of Imidazolium Salt Electrolytes for Electrochemical Capacitor Applications," Journal of the Electrochemical Society, vol. 146, No. 5, 1999, pp. 1687-1695.

H. Matsumoto et al., "Yoyuen oyobi Koon Kagaku (Molten Salt and Pyrochemical)", vol. 44, No. 1, 2001, pp. 7-18, by Molten Salt Committee of the Electrochemical Society of Japan, including English translation of Section 4.2.1 and Section 5.1.

Z.B. Zhou et al., "A New Class of Hydrophobic Ionic Liquids: Trialkyl(2-methoxyethyl)ammonium Perfluoroethyltrifluoroborate," Chemistry Letters, vol. 33, No. 7, 2004, pp. 886-887.

Certificate of Experimental Results, Stella Chemifa Corporation, Dec. 22, 2004.

* cited by examiner

COMPOSITION FOR POLYELECTROLYTES, POLYELECTROLYTES, ELECTRICAL DOUBLE LAYER CAPACITORS AND NONAQUEOUS ELECTROLYTE SECONDARY CELLS

TECHNICAL FIELD

The present invention relates to polymer electrolyte-forming compositions and polymer electrolytes, and also to electrical double-layer capacitors and nonaqueous electrolyte secondary cells in which such polymer electrolytes are used.

BACKGROUND ART

The electrolytes used in electrochemical devices such as electrical double-layer capacitors and nonaqueous electrolyte secondary cells have until now been electrolytes obtained by dissolving a solid electrolyte salt in a nonaqueous solvent or solid electrolytes obtained by rendering such a solution into a solid with a polymer.

Liquid electrolytes lack long-term reliability because non-aqueous electrolyte solutions readily volatilize and are flammable, in addition to which liquid leakage may occur. Solid electrolytes resolve such drawbacks of liquid electrolytes and enable the production process to be simplified. Moreover, they offer the added advantage of making it possible to achieve thinner, smaller, and lighter weight devices. Yet, electrolyte salts lack sufficient solubility in the nonaqueous solvents which are used together with these solid electrolytes, limiting the amount of such salts that may be added. Consequently, the resulting electrolytes have a low ionic conductivity, and electrical double-layer capacitors and non-aqueous electrolyte secondary cells made therewith have a low capacitance or capacity. Moreover, because the electrolyte salt has a low solubility, it readily settles out of solution at low temperatures, which adversely affects the low-temperature properties of devices such as electrical double-layer capacitors.

In searching for a solution to these problems, various electrolytes that use ionic liquids as the electrolyte salt have been studied. Ionic liquids, which are liquid at ambient temperatures, have many desirable characteristics, including (1) absence of a vapor pressure, (2) high heat resistance and broad liquid temperature range, (3) non-flammability, (4) chemical stability, (5) high ionic conductivity, (6) high decomposition voltage, and (7) handleability in air. Such qualities have led recently to a broad and growing recognition of the usefulness of ionic liquids.

Efforts are underway to exploit these attributes by using ionic liquids in various applications, such as solvents for organic synthesis, including solvents for catalytic reactions; highly stable, non-volatile recyclable "green" solvents targeted at material separation and recovery; and novel electrolytes for use in electrochemical devices.

Of these applications, particularly rapid progress is being made in research on the use of ionic liquids as electrolytes for electrical double-layer capacitors or nonaqueous electrolyte secondary cells.

However, such electrolytes, being liquids, may give rise to problems such as liquid leakage that are associated with liquid electrolytes. Recently, to satisfy the desire for higher safety, investigations have also been conducted on solid electrolytes obtained by converting ionic liquids into solids.

For example, JP-A 2002-3478 (Patent Reference 1) discloses an ionic gel obtained by dissolving a polymer in an ionic liquid composed of an imidazolium salt, JP-A 7-118480 (Patent Reference 2) discloses a solid polymer electrolyte obtained by dissolving a polymer having an alkyl quaternary ammonium salt structure in an ionic liquid composed of a nitrogen heterocycle-type quaternary ammonium salt, and JP-A 10-83821 (Patent Reference 3) discloses a solid polymer electrolyte obtained by reacting an imidazolium derivative with monomers to prepare a fused-salt monomer, then polymerizing the fused-salt monomer.

However, when efforts are made to dissolve polymers or monomer compounds in ionic liquids by prior-art methods, dissolution is known to be difficult or impossible owing to the very poor compatibility of the two components. The solid polymer electrolytes disclosed in above Patent References 1 to 3 are also affected by this problem.

In light of these circumstances, one object of the present invention is to provide polymer electrolyte-forming compositions which can be rendered into a polymer without compromising the excellent properties of the ionic liquid, which have an excellent safety and electrical conductivity, and which form electrolytes having a broad potential window. Additional objects of the invention are to provide polymer electrolytes obtained from such compositions, and also electrical double-layer capacitors and nonaqueous electrolyte secondary cells in which such polymer electrolytes are used.

DISCLOSURE OF THE INVENTION

The inventors have conducted extensive investigations in order to achieve the above objects. As a result, they have found that certain alkyl quaternary ammonium salts bearing polymerizable groups have the properties of ionic liquids, and that, by using these salts, a first polymer electrolyte endowed with the excellent properties of the ionic liquid can be obtained. The inventors have also discovered that by adding to the electrolyte-forming composition a quaternary ammonium salt having both an alkyl quaternary ammonium salt structural unit and a reactive unsaturated bond-bearing structural unit, better compatibility is achieved between the ionic liquid, particularly an ionic liquid composed of a certain type of quaternary ammonium salt, and other components of the composition such as reactive double bond-bearing compounds; and that, in this case as well, a second polymer electrolyte can be obtained which retains the excellent properties of the ionic liquid and also has excellent safety and electrical conductivity. The inventors have additionally found that by using these electrolytes, the safety, stability and other characteristics of nonaqueous electrolyte secondary cells and electrical double-layer capacitors can be improved. These discoveries led ultimately to the present invention.

Accordingly, the invention provides the following:

(1) A polymer electrolyte-forming composition characterized by containing (A) a quaternary ammonium salt of general formula (1) below

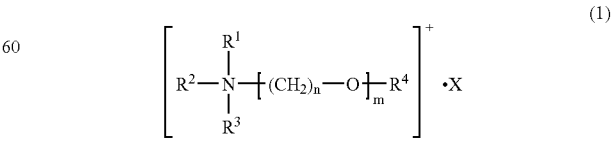

wherein $R^1$ to $R^3$ are each independently an alkyl group of 1 to 5 carbons or a substituent having a reactive unsaturated bond and any two from among $R^1$ to $R^3$ may together form a ring, $R^4$ is methyl, ethyl or a substituent having a reactive unsaturated bond, with the proviso that at least one of $R^1$ to $R^4$ is a substituent having a reactive unsaturated bond, X is a monovalent anion, the letter m is an integer from 1 to 8, and the letter n is an integer from 1 to 4; and (B) an ionic liquid.

(2) The polymer electrolyte-forming composition of (1) above which is characterized in that the ionic liquid (B) is a quaternary ammonium salt of general formula (2) below

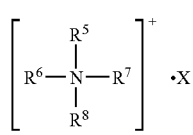

(2)

wherein $R^5$ to $R^8$ are each independently an alkyl of 1 to 5 carbons or an alkoxyalkyl group of the formula R'—O—(CH$_2$)$_n$— (R' being methyl or ethyl, and the letter n being an integer from 1 to 4) and any two from among $R^5$, $R^6$, $R^7$ and $R^8$ may together form a ring, with the proviso that at least one of $R^5$ to $R^8$ is an alkoxyalkyl group of the above formula, and X is a monovalent anion.

(3) The polymer electrolyte-forming composition of (1) or (2) above which is characterized in that the quaternary ammonium salt (A) and/or the ionic liquid (B) has a partial structure of formula (3) below

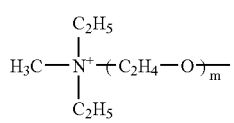

(3)

wherein the letter m is an integer from 1 to 8.

(4) A polymer electrolyte-forming composition characterized by containing (A') a quaternary ammonium salt which has general formula (1) below and has the properties of an ionic liquid

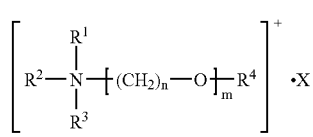

(1)

wherein $R^1$ to $R^3$ are each independently an alkyl group of 1 to 5 carbons or a substituent having a reactive unsaturated bond and any two from among $R^1$ to $R^3$ may together form a ring, $R^4$ is methyl, ethyl or a substituent having a reactive unsaturated bond, with the proviso that at least one of $R^1$ to $R^4$ is a substituent having a reactive unsaturated bond, X is a monovalent anion, the letter m is an integer from 1 to 8, and the letter n is an integer from 1 to 4.

(5) The polymer electrolyte-forming composition of (4) above which is characterized in that the quaternary ammonium salt (A') has a partial structure of formula (3) below

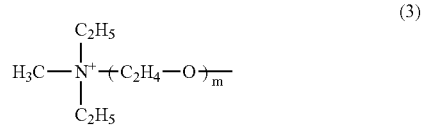

(3)

wherein the letter m is an integer from 1 to 8.

(6) The polymer electrolyte-forming composition of any one of (1) to (5) above which is characterized in that X is at least one selected from among $BF_4^-$, $PF_6^-$, $(CF_3SO_2)_2N^-$, $CF_3SO_3^-$ and $CF_3CO_2^-$.

(7) The polymer electrolyte-forming composition of any one of (1) to (6) above which is characterized by including (C) a compound having a reactive double bond.

(8) The polymer electrolyte-forming composition of any one of (1) to (7) above which is characterized by including (D) an ion-conductive salt.

(9) The polymer electrolyte-forming composition of any one of (1) to (8) above which is characterized by including (E) a straight-chain or branched linear polymeric compound.

(10) A polymer electrolyte which is characterized in that it can be obtained by reacting the polymer electrolyte-forming composition according to any one of (1) to (9) above.

(11) An electrical double-layer capacitor comprising a pair of polarizable electrodes, a separator between the polarizable electrodes, and an electrolyte; which electrical double-layer capacitor is characterized in that the electrolyte is a polymer electrolyte according to (10) above.

(12) A nonaqueous electrolyte secondary cell comprising a positive electrode which contains a lithium-containing compound oxide, a negative electrode which contains a carbonaceous material capable of lithium ion insertion and extraction or contains metallic lithium, a separator between the positive and negative electrodes, and an electrolyte; which nonaqueous electrolyte secondary cell is characterized in that the electrolyte is a polymer electrolyte according to (10) above.

Because the first polymer electrolyte-forming composition of the invention includes a quaternary ammonium salt (A) having both an alkyl quaternary ammonium salt structural unit and a reactive unsaturated bond-bearing structural unit, the compatibility between an ionic liquid (B) that is a quaternary ammonium salt and other components of the composition can be improved. Moreover, because the second polymer electrolyte-forming composition of the invention includes a quaternary ammonium salt (A') having the properties of an ionic liquid, there can be obtained a polymer electrolyte which retains the broad potential window and other excellent properties of the ionic liquid, yet also has an excellent safety and electrical conductivity.

BEST MODE FOR CARRYING OUT THE INVENTION

The invention is described more fully below.

[Polymer Electrolyte-Forming Compositions]

The first polymer electrolyte-forming composition of the invention includes (A) a quaternary ammonium salt of general formula (1) below, and (B) an ionic liquid. In this composition, the quaternary ammonium salt (A) itself may be in the form of a solid or a liquid (ionic liquid).

The second polymer electrolyte-forming composition of the invention includes (A') a quaternary ammonium salt of general formula (1) below which itself exhibits the properties of an ionic liquid.

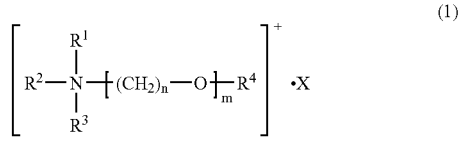

In formula (1), $R^1$ to $R^3$ are each independently an alkyl group of 1 to 5 carbons or a substituent having a reactive unsaturated bond and any two from among $R^1$ to $R^3$ may together form a ring, $R^4$ is methyl, ethyl or a substituent having a reactive unsaturated bond, with the proviso that at least one of $R^1$ to $R^4$ is a substituent having a reactive unsaturated bond, X is a monovalent anion, the letter m is an integer from 1 to 8, and the letter n is an integer from 1 to 4.

In quaternary ammonium salts (A) and (A') of the above general formula (1), examples of alkyls having 1 to 5 carbons include methyl, ethyl, propyl, 2-propyl, butyl and pentyl. However, to provide a structure similar to that of the subsequently described ionic liquid and to increase compatibility, it is preferable for at least one of groups $R^1$ to $R^4$ to be methyl, ethyl or propyl, and especially methyl or ethyl. These ethyl or propyl groups may form a ring with another alkyl group.

The substituent having a reactive unsaturated bond is not subject to any particular limitation, and may be any of various substituents having a reactive double bond or a reactive triple bond. Illustrative examples include groups having an unsaturated bond which can be conjugated with a carbonyl group, such as alkyl acrylate groups and alkyl methacrylate groups; double bond-bearing alkyl groups such as vinyl, allyl and homoallyl; and triple bond-bearing alkyl groups such as propargyl and homopropargyl.

In the above formula, the letter n is an integer from 1 to 4. However, for good ionic liquid formability, it is preferable for n to be 1 or 2. From the standpoint of the physical properties and electrochemical characteristics of the ionic liquid and the availability of the starting materials, it is especially preferable for n to be 2.

The letter m is an integer from 1 to 8, and may be suitably selected according to the properties required of the electrolyte-forming composition. For example, to enable the quaternary ammonium salt to more readily form an ionic liquid and to reduce the number of essential components in the composition so as to simplify its preparation, or to impart rigidity to the composition and the polymer electrolyte obtained therefrom, it is desirable for the letter m to be from 1 to 4, and preferably 1 or 2, so as to give short side chains. On the other hand, to facilitate ion mobility within the composition and the polymer electrolyte obtained therefrom, and thereby enhance electrical conductivity, or to impart flexibility to the composition and the resulting polymer electrolyte, it is desirable for the letter m to be from 4 to 8 so as to give longer side chains.

Exemplary quaternary ammonium salts include those which contain a suitable compound wherein any two groups from among $R^1$ to $R^3$ form a ring, such as an alicyclic compound having an aziridine, azetidine, pyrrolidine or piperidine ring, or an aromatic cyclic compound having a pyridine, pyrrole, imidazole or quinol ring.

As described subsequently, ionic liquids having the partial structure shown below are especially preferred. In compositions which use this ionic liquid, to improve the compatibility, it is preferable for the above quaternary ammonium salts (A) and (A') bearing at least one reactive unsaturated bond to have a partial structure of formula (3) below.

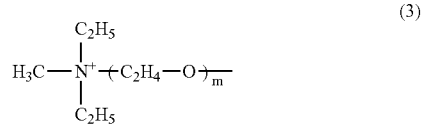

In formula (3), the letter m is an integer from 1 to 8.

It is desirable for the quaternary ammonium salt (A') which has the properties of an ionic liquid to exhibit liquid properties at a temperature not higher than 50° C., preferably not higher than 25° C., and most preferably not higher than 15° C. That is, because nonaqueous electrolyte secondary cells and electrical double-layer capacitors are used at generally from about −10° C. to 50° C., there is no point in using an ionic liquid which is not in a liquid state within this temperature range. Moreover, it is desirable for the temperature at which the salt is in a liquid state to be lower because this broadens the range in the service temperature of the nonaqueous electrolyte secondary cell or electrical double-layer capacitor.

The counteranion X is not subject to any particular limitation. Examples of anions that may be used include $BF_4^-$, $PF_6^-$, $AsF_6^-$, $SbF_6^-$, $AlCl_4^-$, $HSO_4^-$, $ClO_4^-$, $CH_3SO_3^-$, $CF_3SO_3^-$, $CF_3CO_2^-$, $(CF_3SO_2)_2N^-$, $Cl^-$, $Br^-$ and $I^-$. The use of at least one anion selected from among $BF_4^-$, $PF_6^-$, $ClO_4^-$, $CF_3SO_3^-$, $CF_3CO_2^-$, $(C_2F_5SO_2)_2N^-$, $(C_2F_5SO_2)(CF_3SO_2)N^-$ and $(CF_3SO_2)_2N^-$ is preferred. In the case of quaternary ammonium salts (A'), the use of $(C_2F_5SO_2)_2N^-$, $(C_2F_5SO_2)(CF_3SO_2)N^-$ or $(CF_3SO_2)_2N^-$ is preferable for more readily achieving the properties of an ionic liquid. From the standpoint of starting material availability, the use of $(CF_3SO_2)_2N^-$ is especially preferred.

Examples of quaternary ammonium salt (A) that are highly suitable for use in the invention include compounds (4) to (10) below (wherein "Me" stands for methyl and "Et" stands for ethyl). Quaternary ammonium salt (A') having the properties of an ionic liquid is exemplified by Compound (5) and compounds (7) to (10) below.

A common method for synthesizing quaternary ammonium salts (A) and (A') of the invention is described. First, an anion exchange reaction is carried out by reacting an alkyl tertiary ammonium salt having a reactive unsaturated bond with a reagent, such as an alkyl halide, that generates the required anionic species, thereby yielding a quaternary ammonium salt (A) or (A') having both an alkyl quaternary ammonium salt structural unit and a reactive unsaturated bond-bearing structural unit.

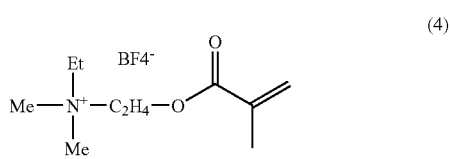

-continued

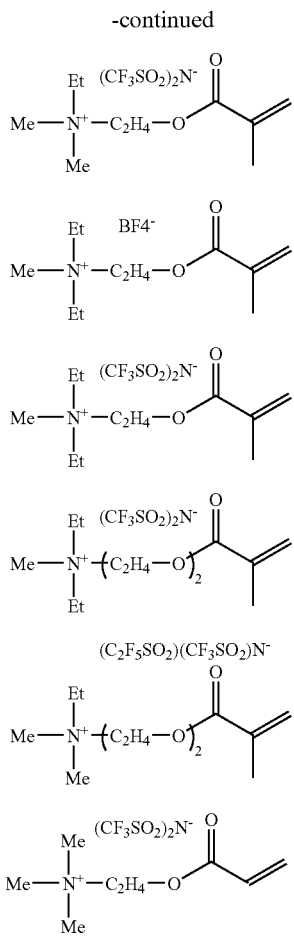

No particular limitation is imposed on the ionic liquid (B) in the invention, although quaternary ammonium salt-type ionic liquids of general formula (2) below are preferred because they exhibit a liquid state at a lower temperature and have a broad potential window.

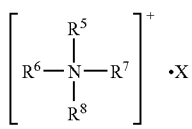

In the formula, $R^5$ to $R^8$ are each independently an alkyl of 1 to 5 carbons or an alkoxyalkyl group of the formula R'—O—(CH$_2$)$_n$— (R' being methyl or ethyl, and the letter n being an integer from 1 to 4) and any two from among $R^5$, $R^6$, $R^7$ and $R^8$ may together form a ring, provided that at least one of $R^5$ to $R^8$ is an alkoxyalkyl group of the above formula. X is a monovalent anion.

Here, the alkyl of 1 to 5 carbons is exemplified by the same groups as mentioned above for quaternary ammonium salt (A). However, from the standpoint of the physical properties and electrochemical characteristics of the ionic liquid, it is preferable for at least one of $R^5$ to $R^8$ to be methyl, ethyl or propyl, and especially methyl or ethyl. These ethyl or propyl groups may form a ring with other alkyl groups.

Examples of alkoxyalkyl groups of the formula R'—O—(CH$_2$)$_n$— include methoxymethyl, ethoxymethyl, methoxyethyl, ethoxyethyl, methoxypropyl, ethoxypropyl, methoxybutyl and ethoxybutyl. The letter n is an integer from 1 to 4. However, for good ionic liquid formability, the letter n is preferably 1 or 2. Taking into consideration also the physical properties and electrochemical characteristics of the ionic liquid, the letter n is most preferably 2.

Compounds in which any two groups from among $R^5$ to $R^8$ together form a ring are exemplified by the same compounds as mentioned above for the quaternary ammonium salt (A) of general formula (1).

A quaternary ammonium salt containing as the substituent at least one methoxyethyl group in which R' is methyl and the letter n is 2 is preferred.

Preferred use can be made of quaternary ammonium salts (A') having the same partial structure as in the above-described quaternary ammonium salt (A) (i.e., the partial structure of formula (3)) because they have desirable properties such as a high electrical conductivity, low viscosity and broad potential window. The use of quaternary ammonium salts of general formula (11) below having as substituents a methyl group, two ethyl groups and an alkoxyethyl group is especially preferred.

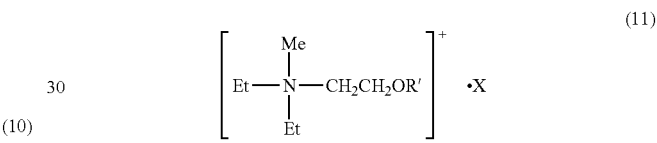

In the formula, R' is methyl or ethyl, X is a monovalent anion, Me stands for methyl and Et stands for ethyl.

The monovalent anion X is not subject to any particular limitation, and is any anion exemplified by the same anions as those mentioned above for the above-described quaternary ammonium salt (A). The use of at least one anion selected from among $BF_4^-$, $PF_6^-$, $ClO_4^-$, $CF_3SO_3^-$, $CF_3CO_2^-$, $(C_2F_5SO_2)_2N^-$, $(C_2F_5SO_2)(CF_3SO_2)N^-$ and $(CF_3SO_2)_2N^-$ is preferred.

Specific examples of ionic liquid (B) that may be suitably used in the invention include compounds (12) to (24) below (wherein Me is methyl and Et is ethyl).

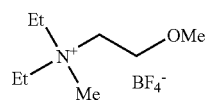

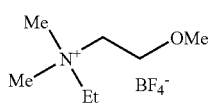

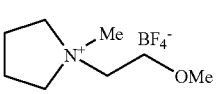

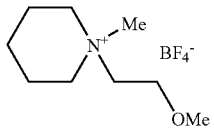

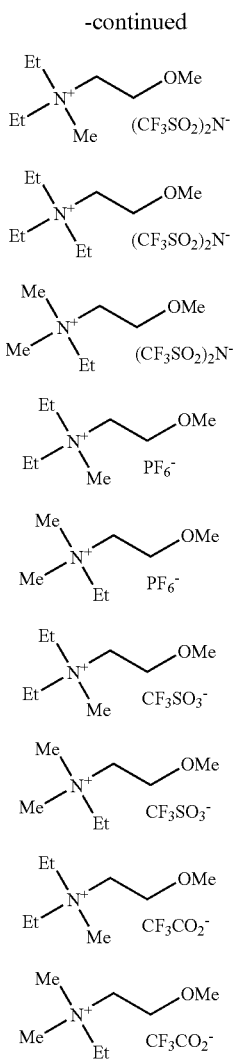

For the same reasons as were given above in connection with the quaternary ammonium salt (A') which exhibits the properties of an ionic liquid, it is advantageous for ionic liquid (B) to be in a liquid state at a temperature not higher than 50° C., preferably not higher than 25° C., and most preferably not higher than 15° C.

Because the quaternary ammonium salt (A') and the ionic liquid (B) having the above-described quaternary ammonium salt structure of the invention are in a liquid state at a lower temperature than the imidazolium ion-containing ionic liquids which have hitherto been used, by employing an electrolyte containing this ionic liquid as the electrolyte in a nonaqueous electrolyte secondary cell or an electrical double-layer capacitor, secondary cells and electrical double-layer capacitors having even better low-temperature characteristics can be obtained.

Also, because the quaternary ammonium salt (A') and the ionic liquid (B) having a quaternary ammonium salt structure have a broader potential window than imidazolium ion-containing ionic liquids known to the prior art, a broader potential window and can more effectively suppress reductive decomposition of the ionic liquid during charging and discharging, there can be obtained an electrolyte which resists deterioration even when charging and discharging are repeatedly carried out. As a result, highly stable secondary cells and electrical double-layer capacitors can be obtained.

A common method for synthesizing the above ionic liquid (B) having a quaternary ammonium salt structure is described. First, a tertiary amine is mixed with a compound such as an alkyl halide or a dialkyl sulfate and reacted under heating, if necessary, to give a quaternary ammonium halide. In cases where a compound having a low reactivity (e.g., an alkoxyethyl halide or an alkoxymethyl halide) is used, reaction under applied pressure, such as in an autoclave, is desirable.

The resulting quaternary ammonium halide is dissolved in an aqueous solvent such as water, then reacted with a reagent that generates the required anionic species, such as tetrafluoroboric acid or tetrafluorophosphoric acid, so as to effect an anion exchange reaction, yielding the quaternary ammonium salt.

In one illustrative method for synthesizing quaternary ammonium tetrafluoroborate, a quaternary ammonium halide is dissolved in water, silver oxide is added and a salt exchange reaction is carried out to form the corresponding quaternary ammonium hydroxide. The product is then reacted with tetrafluoroboric acid, yielding the target compound. This method is effective for synthesizing high-purity quaternary ammonium tetrafluoroborates because the silver halide that arises as a result of salt exchange during formation of the quaternary ammonium hydroxide can easily be removed.

The above-described first and second polymer electrolyte-forming compositions may be used following reaction in this form to effect polymerization, or may be used after adding a polymer thereto to convert it to a solid. However, it is preferable for these compositions to have added thereto a reactive double bond-bearing compound (C) and for the resulting composition to be reacted to convert it into a solid, then used as a solid polymer electrolyte.

In particular, when the first polymer electrolyte-forming composition described above is converted to a solid such as by the addition of a polymer, certain problems are likely to arise, such as a low ability or inability of ionic liquid (B) to dissolve the polymer, or limited dissolution even if dissolution does occur. However, by using a method in which a composition containing also a reactive double bond-bearing compound (C) is reacted and rendered into a polymer to effect solidification, the quaternary ammonium salt (A) and the ionic liquid (B), after being fully dissolved in compound (C), can be converted into a polymer. Thus, a polymer electrolyte having the properties of ionic liquid (B) can easily be obtained.

If the quaternary ammonium salt (A) is not added in this case, the ionic liquid (B) and monomers such as reactive double bond-bearing compound (C) will have a poor compatibility, most likely giving rise to such problems as phase separation, lack of dissolution, dissociation of the components, and/or loss of gel uniformity.

It is thus desirable for the quaternary ammonium salt (A) to have a structure which includes partial structures (substituents) similar to both the ionic liquid (B) and the reactive double bond-bearing compound (C), and preferably the same partial structures (substituents). By using such a quaternary ammonium salt (A), the compatibility between the ionic liquid (B) and the reactive double bond-bearing compound (C) increases further, making it possible to obtain a polymer electrolyte which has the excellent properties of the ionic liquid (B) and is moreover in the form of a clear gel.

Moreover, by reacting the reactive double bond-bearing compound (C) to form a polymer, the physical strength such as shape retention of the resulting polymer electrolyte can be increased.

It is particularly desirable for the compound bearing a reactive double bond on the molecule to have two or more reactive double bonds, because the reaction of such a compound forms a three-dimensional network structure, making it possible to increase even further the shape retaining ability of the resulting electrolyte.

The reactive double bond-bearing compound (C) is not subject to any particular limitation. Illustrative examples include acrylates and methacrylates such as glycidyl methacrylate, glycidyl acrylate, methoxydiethylene glycol methacrylate, methoxytriethylene glycol methacrylate and methoxypolyethylene glycol methacrylate (average molecular weight, 200 to 1,200); and other compounds having one acrylic acid group or methacrylic acid group on the molecule, such as methacryloyl isocyanate, 2-hydroxymethyl methacrylate and N,N-dimethylaminoethyl methacrylate.

Preferred examples of compounds having two or more reactive double bonds include divinylbenzene, divinylsulfone, allyl methacrylate, ethylene glycol dimethacrylate, diethylene glycol dimethacrylate, triethylene glycol dimethacrylate, polyethylene glycol dimethacrylate (average molecular weight, 200 to 1,000), 1,3-butylene glycol dimethacrylate, 1,6-hexanediol dimethacrylate, neopentyl glycol dimethacrylate, polypropylene glycol dimethacrylate (average molecular weight, 400), 2-hydroxy-1,3-dimethacryloxypropane, 2,2-bis[4-(methacryloxyethoxy)phenyl]propane, 2,2-bis[4-(methacryloxyethoxy-diethoxy)phenyl]propane, 2,2-bis[4-(methacryloxyethoxy-polyethoxy)phenyl]propane, ethylene glycol diacrylate, diethylene glycol diacrylate, triethylene glycol diacrylate, polyethylene glycol diacrylate (average molecular weight, 200 to 1,000), 1,3-butylene glycol diacrylate, 1,6-hexanediol diacrylate, neopentyl glycol diacrylate, polypropylene glycol diacrylate (average molecular weight, 400), 2-hydroxy-1,3-diacryloxypropane, 2,2-bis[4-(acryloxyethoxy)phenyl]propane, 2,2-bis[4-(acryloxyethoxy-diethoxy)phenyl]propane, 2,2-bis[4-(acryloxyethoxy-polyethoxy)phenyl]propane, trimethylolpropane triacrylate, trimethylolpropane trimethacrylate, tetramethylolmethane triacrylate, tetramethylolmethane tetraacrylate, water-soluble urethane diacrylate, water-soluble urethane dimethacrylate, tricyclodecane dimethanol acrylate, hydrogenated dicyclopentadiene diacrylate, polyester diacrylate and polyester dimethacrylate.

Of the aforementioned reactive double bond-bearing compounds, especially preferred reactive monomers include the polyoxyalkylene component-bearing diesters of general formula (25) below. The use of such a diester in combination with a polyoxyalkylene component-bearing monoester of general formula (26) below and a triester is recommended.

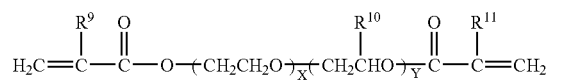
(25)

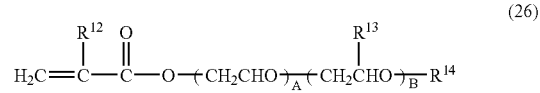
(26)

In formula (25), $R^9$ to $R^{11}$ are each independently a hydrogen atom or an alkyl group having 1 to 6 carbons, and preferably 1 to 4 carbons, such as methyl, ethyl, n-propyl, i-propyl, n-butyl, i-butyl, s-butyl or t-butyl; and X and Y satisfy the condition $X \geq 1$ and $Y \geq 0$ or the condition $X \geq 0$ and $Y \geq 1$. $R^9$ to $R^{11}$ are preferably methyl, ethyl, n-propyl, i-propyl, n-butyl, i-butyl, s-butyl or t-butyl.

In formula (26), $R^{12}$ to $R^{14}$ are each independently a hydrogen atom or an alkyl group having 1 to 6 carbons, and preferably 1 to 4 carbons, such as methyl, ethyl, n-propyl, i-propyl, n-butyl, i-butyl, s-butyl or t-butyl; and A and B satisfy the condition $A \geq 1$ and $B \geq 0$ or the condition $A \geq 0$ and $B \geq 1$. $R^{12}$ to $R^{14}$ are preferably methyl, ethyl, n-propyl, i-propyl, n-butyl, i-butyl, s-butyl or t-butyl.

A preferred example of the compound of above formula (25) is one in which X is 9, Y is 0, and both $R^9$ and $R^{11}$ are $CH_3$. A preferred example of the compound of above formula (26) is one in which A is 2 or 9, B is 0, and both $R^{12}$ and $R^{14}$ are $CH_3$. The triester is preferably trimethylolpropane trimethacrylate.

The relative proportions of the above-described polyoxyalkylene component-bearing diester, monoester and triester are set as appropriate for the length of the polyoxyalkylene components and are not subject to any particular limitation. However, a diester/monoester molar ratio of 0.1 to 2, and especially 0.3 to 1.5, and a diester/triester molar ratio of 2 to 15, and especially 3 to 10, are preferred to enhance the strength of the electrolyte.

The above-described polyoxyalkylene component-bearing diester and polyoxyalkylene component-bearing monoester are exposed, in a mixture together with the above-described quaternary ammonium salt (A) and the ionic liquid (B), to a suitable form of radiation (e.g., UV light, electron beams, x-rays, gamma rays, microwaves, radio-frequency radiation). Alternatively, the mixture is heated to form a three-dimensional crosslinked network structure.

The first and second polymer electrolyte-forming compositions may also have added thereto an ion-conductive salt (D).

The ion-conductive salt (D) may be, for example, any of various known lithium salts capable of being used in nonaqueous electrolyte secondary-cells. To ensure such properties as versatility, good solubility in the ionic liquid and a high degree of dissociation, the use of $LiBF_4$, $LiPF_6$, $Li(CF_3SO_2)_2N$, $LiCF_3SO_3$ or $LiCF_3CO_2$ is especially preferred.

The content of lithium salt in the above electrolyte-forming compositions is not subject to any particular limitation, although the content is generally 0.05 to 3 mol/L, and preferably 0.1 to 2 mol/L. Too low a lithium salt concentration may result in a higher cell impedance, which make charging and discharging at a large current impossible. On the other hand, a lithium salt concentration which is too high increases the liquid viscosity, which may make battery and capacitor production difficult.

The first and second polymer electrolyte-forming compositions described above may also have added thereto (E) a straight-chain or branched linear polymeric compound.

When the nonaqueous electrolyte-forming compositions of the invention include as the above-described reactive double-bond-bearing compound (C) a compound having two or more reactive double bonds and include also a linear polymeric compound (E), there can be obtained an electrolyte having a semi-interpenetrating polymer network (semi-IPN) structure in which the molecular chains of the linear polymeric compound (E) are intertwined with the three-dimensional network structure of the polymer formed by crosslinkage of the compound having two or more reactive double bonds. The shape retention and strength of the electrolyte can thus be further increased, and its adhesive properties and ionic conductivity also enhanced.

The straight-chain or branched linear polymeric compound (E) is not subject to any particular limitation so long as it is a linear polymer. However, a compound having a high compatibility with the ionic liquid (B) is preferred. Specifically, polar polymers which are polymers having a donor-type structure and also have amorphous regions and a low glass transition point are preferred. Preferred examples of such linear polymeric compounds include (a) hydroxyalkyl polysaccharide derivatives, (b) oxyalkylene branched polyvinyl alcohol derivatives, (c) polyglycidol derivatives, (d) cyano-substituted monovalent hydrocarbon group-bearing polyvinyl alcohol derivatives, and (e) thermoplastic polyurethanes.

Illustrative examples of (a) hydroxyalkyl polysaccharide derivatives include: (1) hydroxyethyl polysaccharides prepared by reacting ethylene oxide with a naturally occurring polysaccharide such as cellulose, starch or pullulan; (2) hydroxypropyl polysaccharides prepared by reacting propylene oxide with the above naturally occurring polysaccharides; and (3) dihydroxypropyl polysaccharides prepared by reacting glycidol or 3-chloro-1,2-propanediol with the above naturally occurring polysaccharides. Hydroxyalkyl polysaccharide derivatives in which some or all of the hydroxyl groups on these hydroxyalkyl polysaccharides are capped with an ester-bonded or ether-bonded substituent are preferred.

The above hydroxyalkyl polysaccharides have a molar substitution of 2 to 30, and preferably 2 to 20. At the molar substitution of less than 2, the lithium salt dissolving ability of the hydroxyalkyl polysaccharide may become so low as to make it unsuitable for use.

Oxyalkylene branched polyvinyl alcohol derivatives (b) suitable for use as the polymeric compound include polymeric compounds which bear on the molecule polyvinyl alcohol units of general formula (27) below, which have an average degree of polymerization of at least 20, and in which some or all of the hydroxyl groups on the polyvinyl alcohol units are substituted with oxyalkylene-bearing groups having an average molar substitution of at least 0.3.

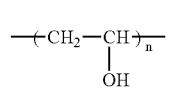

(27)

In formula (27), the letter n is preferably from 20 to 10,000.

Because this type of polymeric compound has a high oxyalkylene fraction, it has the ability to dissolve a large amount of salt. In addition, the molecule contains many oxyalkylene segments which permit the movement of ions, resulting in a high ion mobility. This type of polymeric compound is thus capable of exhibiting a high ionic conductivity. Moreover, these polymeric compounds have a high tackiness. Accordingly, they act as a binder component and are capable of firmly bonding the positive and negative electrodes.

Examples of polymeric compounds of above formula (27) include [1] polymeric compounds obtained by reacting a polyvinyl alcohol unit-containing polymeric compound with an oxirane compound such as ethylene oxide, propylene oxide or glycidol (e.g., dihydroxypropylated polyethylene vinyl alcohol, propylene oxide-modified polyvinyl alcohol); and [2] polymeric compounds obtained by reacting a polymeric compound having polyvinyl alcohol units with a polyoxyalkylene compound having terminal hydroxy-reactive substituents.

Here, the polyvinyl alcohol unit-bearing polymeric compound is a polymeric compound which has polyvinyl alcohol units on the molecule, which has a number-average degree of polymerization of at least 20, preferably at least 30, and most preferably at least 50, and in which some or all of the hydroxyl groups on the polyvinyl alcohol units are substituted with oxyalkylene-bearing groups. For the sake of handleability, the upper limit in the number-average degree of polymerization in this case is preferably not more than 2,000, more preferably not more than 500, and most preferably not more than 200.

It is most preferable for the above-described polyvinyl alcohol unit-bearing polymeric compound to have a number-average degree of polymerization within the above range and to be a homopolymer in which the fraction of polyvinyl alcohol units in the molecule is at least 98 mol %. However, the polyvinyl alcohol unit-bearing polymeric compound is not limited to the above, and may be one which has a number-average degree of polymerization within the above range and a polyvinyl alcohol fraction of preferably at least 60 mol %, and more preferably at least 70 mol %. Illustrative examples of such compounds that may be used include polyvinyl formals in which some of the hydroxyl groups on the polyvinyl alcohol have been converted to formal, modified polyvinyl alcohols in which some of the hydroxyl groups on the polyvinyl alcohol have been converted to alkyls, poly(ethylene vinyl alcohols), partially saponified polyvinyl acetates, and other modified polyvinyl alcohols.

This polymeric compound is one in which some or all of the hydroxyl groups on the above-described polyvinyl alcohol units are substituted with oxyalkylene-containing groups having an average molar substitution of at least 0.3 (moreover, some of the hydrogen atoms on these oxyalkylene groups may be substituted with hydroxyl groups). Preferably at least 30 mol %, and most preferably at least 50 mol %, of the hydroxyl groups are substituted in this way.

The above-mentioned polyglycidol derivative (c) contains units of formula (28) (referred to hereinafter as "A units")

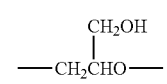

(28)

and units of formula (29) (referred to hereinafter as "B units")

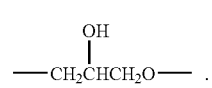

(29)

The ends of the molecular chain are capped with specific substituents.

The polyglycidol can be prepared by polymerizing glycidol or 3-chloro-1,2-propanediol, although it is generally preferable to carry out polymerization from glycidol as the starting material and using a basic catalyst or a Lewis acid catalyst.

The total number of A and B units on the polyglycidol molecule is at least two, preferably at least six, and most preferably at least ten. There is no particular upper limit, although it is generally preferable for the total number of such units to not exceed about 10,000. The total number of these respective units may be set as appropriate based on such considerations as the flowability and viscosity required of the polyglycidol. The ratio of A units to B units in the molecule, expressed as A/B, is within a range of 1/9 to 9/1, and preferably 3/7 to 7/3. There is no particular order to the arrangement of A and B units; any combination is possible.

The polyglycidol has a polyethylene glycol equivalent weight-average molecular weight (Mw), as determined by gel permeation chromatography (GPC), within a range of preferably 200 to 730,000, more preferably 200 to 100,000, and most preferably 600 to 20,000. The dispersity (Mw/Mn) is preferably 1.1 to 20, and most preferably 1.1 to 10.

These polymeric compounds (a) to (c) may be hydroxyl-capped polymer derivatives in which some or all, and preferably at least 10 mol %, of the hydroxyl groups on the molecule are capped with one or more type of monovalent substituent selected from among halogen atoms, substituted or unsubstituted monovalent hydrocarbon groups having 1 to 10 carbons, $R^{15}CO$— groups (wherein R's is a substituted or unsubstituted monovalent hydrocarbon group of 1 to 10 carbons), $R^{15}_3Si$— groups (wherein $R^{15}$ is as defined above), amino groups, alkylamino groups and phosphorus atom-containing groups.

Illustrative examples of the substituted or unsubstituted monovalent hydrocarbon groups having 1 to 10 carbons include alkyl groups such as methyl, ethyl, propyl, isopropyl, t-butyl and pentyl, aryl groups such as phenyl and tolyl, aralkyl groups such as benzyl, alkenyl groups such as vinyl, and any of the foregoing in which some or all of the hydrogen atoms have been substituted with halogen atoms, cyano-groups, hydroxyl-groups or amino groups. Any one or combination of two or more of these types of groups may be used.

Capping the hydroxyl groups on the above polymeric compounds (a) to (c) with highly polar substituents increases the polarity (and thus the relative permittivity) of the polymer matrix, making it possible to prevent the decline in conductivity which readily arises in a low relative permittivity polymer matrix due to the recombination of dissociated cations and counteranions. Moreover, when capping is done using substituents that have fire-retarding and hydrophobic properties, the polymeric compound can be imparted with desirable characteristics such as hydrophobicity and fire retardance.

To increase the relative permittivity of above polymeric compounds (a) to (c), the oxyalkylene chain-bearing polymeric compounds (a) to (c) are reacted with a hydroxy-reactive compound so as to cap the hydroxyl groups on these polymeric compounds with highly polar substituents.

Although the highly polar substituents used for this purpose are not subject to any particular limitation, neutral substituents are preferable to ionic substituents. Exemplary substituents include substituted and unsubstituted monovalent hydrocarbon groups of 1 to 10 carbons, and $R^{15}CO$— groups (wherein $R^{15}$ is as defined above). If necessary, capping may also be carried out with other suitable substituents, such as amino groups or alkylamino groups.

To confer polymeric compounds (a) to (c) with hydrophobic properties and fire retardance, the hydroxyl groups on the above polymeric compounds may be capped with, for example, halogen atoms, $R^{15}_3Si$— groups (wherein $R^{15}$ is as defined above) or phosphorus-containing groups.

Examples of suitable $R^{15}_3Si$— groups include those in which $R^{15}$ represents the same substituted or unsubstituted monovalent hydrocarbon groups having 1 to 10 carbons, and preferably 1 to 6 carbons, as above. $R^{15}$ preferably stands for alkyl groups. Trialkylsilyl groups, and especially trimethylsilyl groups, are preferred.

Additional examples of suitable substituents include amino groups, alkylamino groups and phosphorus atom-containing groups.

The proportion of end groups capped with the above substituents is at least 10 mol %, preferably at least 50 mol %, and most preferably at least 90 mol %. It is even possible to cap substantially all the end groups with the above substituents, representing a capping ratio of about 100 mol %.

The above-mentioned cyano-substituted monovalent hydrocarbon group-bearing polyvinyl alcohol derivative (d) is preferably a polymeric compound which bears on the molecule polyvinyl alcohol units of above general formula (27), which has an average degree of polymerization of at least 20, and in which some or all of the hydroxyl groups on the polyvinyl alcohol units are substituted with cyano-substituted monovalent hydrocarbon groups.

Because this polymeric compound has relatively short side chains, the viscosity of the electrolyte can be held to a low level.

Examples of such polymeric compounds include polyvinyl alcohols in which some or all of the hydroxyl groups are substituted with groups such as cyanoethyl, cyanobenzyl or cyanobenzoyl. Cyanoethyl-substituted polyvinyl alcohols are especially preferred because the side chains are short.

Various known methods may be used to substitute the hydroxyl groups on the polyvinyl alcohol with cyano-substituted monovalent hydrocarbon groups.

The above-mentioned thermoplastic polyurethane (e) is preferably a thermoplastic polyurethane prepared by reacting (1) a polyol compound, (2) a polyisocyanate compound and, if necessary, (3) a chain extender.

Suitable thermoplastic polyurethanes include not only polyurethane resins having urethane bond, but also polyurethane-urea resins having both urethane bond and urea bond.

The polyol compound (1) is preferably a polyether polyol, a polyester polyol, a polyester polyether polyol, a polyester polycarbonate polyol, a polycaprolactone polyol, or a mixture thereof.

This poly compound has a number-average molecular weight of preferably 1,000 to 5,000, and more preferably 1,500 to 3,000. A polyol compound having too small a number-average molecular weight may lower the physical properties of the resulting thermoplastic polyurethane resin film, such as the heat resistance and tensile elongation percentage. On the other hand, too large a number-average molecular weight increases the viscosity during synthesis, which may lower the production stability of the thermoplastic polyurethane resin being prepared. The number-average molecular weights used here in connection with polyol compounds are all calculated based on the hydroxyl values measured in accordance with JIS K1577.

Illustrative examples of the polyisocyanate compound (2) include aromatic diisocyanates such as tolylene diisocyanate, 4,4'-diphenylmethane diisocyanate, p-phenylene diisocyanate, 1,5-naphthylene diisocyanate and xylylene diisocyanate; and aliphatic or alicyclic diisocyanates such as hexamethylene diisocyanate, isophorone diisocyanate, 4,4'-dicyclohexylmethane diisocyanate and hydrogenated xylylene diisocyanate.

The chain extender (3) is preferably a low-molecular-weight compound having a molecular weight of not more than 300 and bearing two active hydrogen atoms capable of reacting with isocyanate groups.

Various known compounds may be used as such low-molecular-weight compounds. Illustrative examples include aliphatic diols such as ethylene glycol, propylene glycol and 1,3-propanediol; aromatic or alicyclic diols such as 1,4-bis(β-hydroxyethoxy)benzene, 1,4-cyclohexanediol and bis(β-hydroxyethyl) terephthalate; diamines such as hydrazine, ethylenediamine, hexamethylenediamine and xylylenediamine; and amino alcohols such as adipoyl hydrazide. Any one or combinations of two or more of these may be used.

The thermoplastic polyurethane typically includes 5 to 200 parts by weight, and preferably 20 to 100 parts by weight, of the polyisocyanate compound (2) and 1 to 200 parts by weight, and preferably 5 to 100 parts by weight, of the chain extender (3) per 100 parts by weight of the polyol compound (1).

The polymer electrolyte of the invention can be obtained by conversion to a polymer or solidification (gelation) of the above-described first and second polymer electrolyte-forming compositions such as with a polymerization reaction.

That is, the above-described composition containing quaternary ammonium salt (A) having at least one reactive unsaturated bond-containing substituent and ionic liquid (B), or the above-described composition containing quaternary ammonium salt (A'), can be converted into a polymer by exposure to radiation such as UV light, electron beams, x-rays, gamma rays, microwaves or radio-frequency radiation, or by heating, so as to give an ionic liquid-containing polymer electrolyte.

In cases where a quaternary ammonium salts (A) or (A') containing two or more reactive unsaturated bond-containing substituents is used, a polymer electrolyte having a three-dimensional network structure can be obtained. The formation of such a three-dimensional network structure enables a polymer electrolyte of increased shape retention to be achieved.

By also including in the composition, along with the above components, a compound (C) having a reactive double bond on the molecule and heating the composition or exposing it to radiation such as UV light, there can be obtained a polymer electrolyte having a three-dimensional network structure, and thus greater physical strength.

If either the quaternary ammonium salt (A or A') having a reactive unsaturated bond-containing substituent or compound (C) having a reactive double bond on the molecule is a compound having two or more reactive unsaturated (double) bonds, a polymer electrolyte having a three-dimensional network structure can be obtained.

Moreover, if the above quaternary ammonium salt (A or A') and/or compound (C) has at least two reactive unsaturated (double) bonds, by also adding to a composition containing these components a linear polymeric compound (E) and carrying out irradiation such as with UV light or heating in the same way as described above, there can be obtained a polymer electrolyte having a three-dimensional crosslinked network (semi-IPN) structure in which the molecular chains of the linear polymeric compound are intertwined with the three-dimensional network structure formed by reaction or polymerization of the compound having on the molecule at least two reactive unsaturated (double) bonds. The formation of such a semi-IPN structure can further enhance the shape retention and strength of the electrolyte, and can also increase its adhesive properties and ionic conductivity.

The above polymerization reaction is preferably a radical polymerization reaction. A polymerization initiator is generally added when the polymerization reaction is carried out. No particular limitation is imposed on the initiator (catalyst). Any of various known polymerization initiators such as those shown below may be used.

Illustrative examples include photopolymerization initiators such as acetophenone, trichloroacetophenone, 2-hydroxy-2-methylpropiophenone, 2-hydroxy-2-methylisopropiophenone, 1-hydroxycyclohexyl ketone, benzoin ether, 2,2-diethoxyacetophenone and benzyl dimethyl ketal; high-temperature thermal polymerization initiators such as cumene hydroperoxide, t-butyl hydroperoxide, dicumyl peroxide and di-t-butyl peroxide; conventional thermal polymerization initiators such as benzoyl peroxide, lauroyl peroxide, persulfates, 2,2'-azobis(2,4-dimethylvaleronitrile), 2,2'-azobis(4-methoxy-2,4-dimethylvaleronitrile) and 2,2'-azobisisobutyronitrile; low-temperature thermal polymerization initiators (redox initiators) such as hydrogen peroxide-ferrous salts, persulfate-acidic sodium sulfite, cumene hydroperoxide-ferrous salts and benzoyl peroxide-dimethylaniline; and also peroxide-organometallic alkyls, triethylboron, diethylzinc, and oxygen-organometallic alkyls.

These initiators may be used alone or as a mixture of two or more thereof. The initiator is typically added in an amount of 0.1 to 1 part by weight, and preferably 0.1 to 0.5 part by weight, per 100 parts by weight of the polymer electrolyte-forming composition. The addition of less than 0.1 part by weight may result in a considerable decline in the polymerization rate. On the other hand, the addition of more than 1 part by weight increases the number of reaction initiation sites and may result in the formation of a low-molecular-weight compound.

As noted above, because the first polymer electrolyte-forming composition of the invention includes a quaternary ammonium salt (A) having both an alkyl quaternary ammonium salt structural unit and a reactive unsaturated bond-bearing structural unit, the compatibility with constituents of the composition, including the ionic liquid (B) and the reactive double bond-bearing compound (C) which is added if necessary, can be improved. The second polymer electrolyte-forming composition of the invention includes a quaternary ammonium salt (A') having the properties of an ionic liquid. Therefore, when electrolyte-forming compositions containing these components are used, polymer electrolytes can be obtained which retain the excellent properties of ionic liquids, such as a broad potential window, and also have an excellent safety and electrical conductivity. As a result, the safety, stability and other properties of the nonaqueous electrolyte secondary cells and electrical double-layer capacitors can be improved.

[Electrical Double-Layer Capacitor]

The electrical double-layer capacitor according to this invention is an electrical double-layer capacitor having a pair of polarizable electrodes, a separator between the polarizable electrodes, and an electrolyte. The electrolyte is the above-described polymer electrolyte.

The polarizable electrodes used here may be ones obtained by coating a current collector with a polarizable electrode composition containing a carbonaceous material and a binder polymer.

The carbonaceous material is not subject to any particular limitation. Illustrative examples include carbonaceous materials prepared by the carbonization of a suitable starting material, or by both carbonization and subsequent activation of the carbonized material to yield activated carbon.

Examples of suitable starting materials include plant-based materials such as wood, sawdust, coconut shells and pulp spent liquor; fossil fuel-based materials such as coal and petroleum fuel oil, as well as fibers spun from coal or petroleum pitch obtained by the thermal cracking of such fossil fuel-based materials or from tar pitch; and synthetic polymers, phenolic resins, furan resins, polyvinyl chloride resins, polyvinylidene chloride resins, polyimide resins, polyamide resins, polycarbodiimide resins, liquid-crystal polymers, plastic waste and reclaimed tire rubber.

The method of activation is not subject to any particular limitation. Any of various methods, such as chemical activation and steam activation, may be used. However, activated carbons prepared by chemical activation using potassium hydroxide are especially preferred because they tend to provide a larger capacitance than steam-activated product.

The carbonaceous material used in the invention may be in any of various forms, including shredded material, granulated material, pellets, fibers, felt, woven fabric or sheet.

A conductive material may be added to the carbonaceous material. The conductive material may be any suitable material capable of conferring electrical conductivity to the carbonaceous material. Illustrative, non-limiting, examples include carbon black, Ketjenblack, acetylene black, carbon whiskers, carbon fibers, natural graphite, artificial graphite, titanium oxide, ruthenium oxide, and metallic fibers such as those made of aluminum and nickel. Any one or combinations of two or more thereof may be used. Of these, Ketjenblack and acetylene black, which are both types of carbon black, are preferred.

The average particle size of the conductive material, though not subject to any particular limitation, is preferably 10 nm to 10 μm, more preferably 10 to 100 nm, and even more preferably 20 to 40 nm. It is especially advantageous for the conductive material to have an average particle size which is from 1/5000 to 1/2, and preferably from 1/1000 to 1/10, the average particle size of the carbonaceous material.

The amount of conductive material added is not subject to any particular limitation, although an amount of from 0.1 to 20 parts by weight, and preferably from 0.5 to 10 parts by weight, per 100 parts by weight of the carbonaceous material is desirable for achieving a good electrostatic capacitance and imparting electrical conductivity.

The binder polymer mentioned above may be any polymer capable of being used in the applications of concern here. For example, use can be made of various known binder polymers, such as polytetrafluoroethylene, polyvinylidene fluoride, carboxymethyl cellulose, fluoroolefin copolymer-type crosslinked polymers, polyvinyl alcohol, polyacrylic acid, polyimide, petroleum pitch, coal pitch and phenolic resins.

It is especially preferable to use as the binder polymer (I) a thermoplastic resin having a swelling ratio, as defined by the formula below, in a range of 150 to 800%, (II) a fluoropolymer material, or a combination of two or more polymers of types (I) and (II).

The above thermoplastic resin (I) has a swelling ratio, as determined from the formula indicated below, within a range of 150 to 800%, preferably 250 to 500%, and most preferably 250 to 400%.

Swelling ratio (%) =

$$\frac{\text{Weight in grams of swollen thermoplastic resin after 24 hours immersion in electrolyte solution at } 20° \text{ C. (g)}}{\text{Weight in grams of thermoplastic resin before immersion in electrolyte solution at } 20° \text{ C. (g)}} \times 100$$

A thermoplastic resin containing units of general formula (30) below

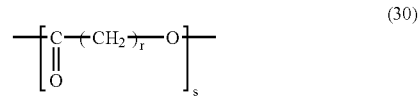

wherein the letter r is 3 to 5 and the letter s is an integer ≧5, may be used as the binder polymer of type (I) above.

Preferred examples of fluoropolymer materials (II) that may be used as the binder polymer include polyvinylidene fluoride (PVDF), vinylidene fluoride-hexafluoropropylene copolymers (P(VDF-HFP)) and vinylidene fluoride-chlorotrifluoroethylene copolymers (P(VDF-CTFE)). Of these, fluoropolymers having a vinylidene fluoride content of at least 50 wt %, and especially at least 70 wt %, are preferred. The upper limit in the vinylidene fluoride content of the fluoropolymer is about 97 wt %.

The weight-average molecular weight of the fluoropolymer is not subject to any particular limitation, although the weight-average molecular weight is preferably 500,000 to 2,000,000, and most preferably 500,000 to 1,500,000. Too low a weight-average molecular weight may result in an excessive decline in physical strength.

It is preferable for these binder polymers to be added in an amount of 0.5 to 20 parts by weight, and especially 1 to 10 parts by weight, per 100 parts by weight of the carbonaceous material.

No particular limitation is imposed on the method of preparing the polarizable electrode composition. For example, the composition may be prepared by rendering the above-described carbonaceous material and binder polymer into the form of a solution. If necessary, a solvent may be added to this solution.

The resulting polarizable electrode composition is applied onto a current collector to form a polarizable electrode. The method of application is not subject to any particular limitation. Any known method of application, such as one involving the use of a doctor blade or an air knife, may be suitably employed.

The current collectors used for this purpose may be any positive and negative electrode current collectors commonly employed in electrical double-layer capacitors. The positive electrode current collector is preferably aluminum foil or aluminum oxide, and the negative electrode current collector is preferably copper foil, nickel foil, or a metal foil covered on the surface with a copper plating film or a nickel plating film.

The foils making up the respective current collectors may be in any of various shapes, including thin foils, flat sheets, and perforated, stampable sheets. The foil has a thickness of generally about 1 to 200 μm. Taking into account such characteristics as the density of the activated carbon as a portion of the overall electrode and the electrode strength, a thickness of 8 to 100 μm, and especially 8 to 30 μm, is preferred.

Alternatively, the polarizable electrodes can be produced by melting and blending the polarizable electrode composition, then extruding the blend as a film.

A conductive material may be added to the above-described activated carbon. The conductive material may be any suitable material capable of conferring electrical conductivity to the activated carbon. Illustrative, non-limiting, examples include carbon black, Ketjenblack, acetylene black, carbon whiskers, carbon fibers, natural graphite, artificial graphite, titanium oxide, ruthenium oxide, and metallic fibers such as those made of aluminum and nickel. Any one or combinations of two or more thereof may be used. Of these, Ketjenblack and acetylene black, which are both types of carbon black, are preferred.

The average particle size of the conductive material, though not subject to any particular limitation, is preferably 10 nm to 10 μm, more preferably 10 to 100 nm, and even more preferably 20 to 40 nm. It is especially advantageous for the conductive material to have an average particle size which is from 1/5000 to 1/2, and preferably from 1/1000 to 1/10, the average particle size of the activated carbon.

The amount of conductive material added is not subject to any particular limitation, although an amount of from 0.1 to 20 parts by weight, and preferably 0.5 to 10 parts by weight, per 100 parts by weight of the activated carbon is desirable for achieving a good electrostatic capacitance and imparting electrical conductivity.

The separator may be one that is commonly used in electrical double-layer capacitors. Illustrative examples include polyolefin nonwoven fabric, polytetrafluoroethylene porous film, kraft paper, sheet laid from a blend of rayon fibers and sisal fibers, manila hemp sheet, glass fiber sheet, cellulose-based electrolytic paper, paper made from rayon fibers, paper made from a blend of cellulose and glass fibers, and combinations thereof in the form of multilayer sheets.

The electrical double-layer capacitor of the invention can be assembled by stacking, fan-folding or winding an electrical double-layer capacitor assembly composed of the above-described pair of polarizable electrodes with a separator therebetween. The capacitor assembly is placed within a capacitor housing such as a can or a laminate pack, following which the housing is filled with the above-described polymer electrolyte-forming composition then mechanically sealed if it is a can or heat-sealed if it is a laminate pack. The composition may additionally be reacted to effect curing.

The resulting electrical double-layer capacitor of the invention can be operated at a high capacity and a high current without comprising such desirable characteristics as its excellent charge/discharge efficiency, high energy density, high power density and long life. Moreover, it has a broad service temperature range and excellent safety without undesirable effects such as fluid leakage.

The electrical double-layer capacitors of the invention are highly suitable for use as a memory backup power supply for cell phones, notebook computers and portable remote terminals, as a power supply for cell phones and portable acoustic devices, as an uninterruptible power supply for personal computers and other equipment, and as various types of low-current electrical storage devices such as load leveling power supplies used in combination with solar power generation and wind power generation. Moreover, electrical double-layer capacitors capable of being charged and discharged at a high current are suitable for use as high-current electrical storage devices in applications that require a large current, such as electric cars and electrical power tools.

[Nonaqueous Electrolyte Secondary Cells]

The secondary cell according to this invention is a secondary cell having a positive electrode which contains a lithium-containing compound oxide, a negative electrode containing a carbonaceous material capable of lithium ion insertion and extraction or containing metallic lithium, and a separator between the positive and negative electrodes. The electrolyte is the above-described polymer electrolyte.

The positive electrode may be one that is produced by coating both the front and back sides or just one side of a positive electrode current collector with a positive electrode binder composition composed primarily of a binder polymer and a positive electrode active material.

Alternatively, a positive electrode binder composition composed primarily of a binder polymer and a positive electrode active material may be melted and blended, then extruded as a film to form the positive electrode.

The binder polymer may be any polymer capable of being used in the applications of concern here, such as the binder polymers described above in connection with electrical double-layer capacitors.

The positive electrode current collector may be made of a suitable material such as stainless steel, aluminum, titanium, tantalum or nickel. Of these, aluminum foil or aluminum oxide foil is especially preferred both in terms of performance and cost. This current collector may be used in any of various forms, including foil, expanded metal, sheet, foam, wool, or a three-dimensional structure such as a net.

In the invention, lithium ion-containing chalcogen compounds (lithium-containing compound oxides) may be used as the above positive electrode active material.

Specific examples of such lithium ion-containing chalcogen compounds (lithium-containing compound oxides) include $LiCoO_2$, $LiMnO_2$, $LiMn_2O_4$, $LiMo_2O_4$, $LiV_3O_8$, $LiNiO_2$ and $Li_xNi_yM_{1-y}O_2$ (wherein M is one or more metal element selected from among cobalt, manganese, titanium, chromium, vanadium, aluminum, tin, lead and zinc; $0.05 \leq x \leq 1.10$; and $0.5 \leq y \leq 1.0$).

In addition to the binder resin and the positive electrode active material described above, if necessary, the binder composition for the positive electrode may include also an electrically conductive material. Illustrative examples of the conductive material include carbon black, Ketjenblack, acetylene black, carbon whiskers, carbon fibers, natural graphite and artificial graphite.

The positive electrode binder composition typically includes 1,000 to 5,000 parts by weight, and preferably 1,200 to 3,500 parts by weight, of the positive electrode active material and 20 to 500 parts by weight, and preferably 50 to 400 parts by weight, of the conductive material per 100 parts by weight of the binder polymer.

The negative electrode may be a negative electrode composed of lithium metal or a negative electrode produced by coating both the front and back sides or just one side of a negative electrode current collector with a negative electrode binder composition composed primarily of a binder polymer and a negative electrode active material. The same binder polymer may be used as in the positive electrode.

Alternatively, the negative electrode binder composition composed primarily of a binder polymer and a negative electrode active material may be melted and blended, then extruded as a film to form a negative electrode.

The negative electrode current collector may be made of a suitable material such as copper, stainless steel, titanium or nickel. Of these, copper foil or a metal foil whose surface is covered with a copper plating film is especially preferred both in terms of performance and cost. The current collector used may be in any of various forms, including foil, expanded metal, sheet, foam, wool, or a three-dimensional structure such as a net.

The negative electrode active material is a carbonaceous material which reversibly inserts and extracts lithium ions.

This carbonaceous material used may be a carbonaceous material such as a non-graphitizable carbonaceous material or a graphite material. Specific examples of carbonaceous materials that may be used include pyrolytic carbon, cokes (e.g., pitch coke, needle coke, petroleum coke), graphites, glassy carbons, fired organic polymeric materials (materials such as phenolic resins or furan resins that have been carbonized by firing at a suitable temperature), carbon fibers, and activated carbon.

If necessary, a conductive material may be added to the negative electrode binder composition as well. Examples of suitable conductive materials include the same materials as those mentioned above in connection with the positive electrode binder.

The negative electrode binder composition typically includes 500 to 1,700 parts by weight, preferably 700 to 1,300 parts by weight, of the negative electrode active material and 0 to 70 parts by weight, preferably 0 to 40 parts by weight, of the conductive material per 100 parts by weight of the binder polymer.

The above-described negative electrode binder compositions and positive electrode binder compositions generally are used in the form of a paste after the addition of a dispersing medium. Suitable dispersing media include polar solvents such as N-methyl-2-pyrrolidone (NMP), dimethylformamide, dimethylacetamide and dimethylsulfamide. The dispersing medium is typically added in an amount of about 30 to 300 parts by weight per 100 parts by weight of the positive electrode or negative electrode binder composition.

No particular limitation is imposed on the method of shaping the positive and negative electrodes as thin films, although it is preferable to apply the composition by a suitable means such as roller coating with an applicator roll, screen coating, doctor blade coating, spin coating or bar coating so as to form an active material layer having a uniform thickness when dry of 10 to 200 μm, and especially 50 to 150 μm.

Illustrative, non-limiting, examples of the separator between the positive and negative electrodes include polyethylene nonwoven fabric, polypropylene nonwoven fabric, polyester nonwoven fabric, polytetrafluoroethylene porous film, kraft paper, sheet laid from a blend of rayon fibers and sisal fibers, manila hemp sheet, glass fiber sheet, cellulose-based electrolytic paper, paper made from rayon fibers, paper made from a blend of cellulose and glass fibers, and combinations thereof in the form of multilayer sheets.

The secondary cell of the invention can be assembled by stacking, fan-folding or winding a cell assembly composed of the separator disposed between the positive and negative electrodes. The cell assembly is placed within a battery housing such as a battery can or a laminate pack, following which the housing is filled with the above-described polymer electrolyte-forming composition, then mechanically sealed it is a can or heat-sealed if it is a laminate pack. The composition may additionally be reacted to effect curing.

The resulting nonaqueous electrolyte secondary cell of the invention can be operated at a high capacity and a high current without compromising such desirable characteristics as its excellent charge-discharge efficiency, high energy density, high output density and long life. Moreover, the cell has a broad service temperature range and excellent safety without undesirable effects such as fluid leakage.

The nonaqueous electrolyte secondary cell of the invention lends itself well to use in a variety of applications, including main power supplies and memory backup power supplies for portable electronic equipment such as video cameras, notebook computers, cell phones and PHS ("personal handyphone system") devices, uninterruptible power supplies for equipment such as personal computers, in electric cars and hybrid cars, and together with solar cells as energy storage systems for solar power generation.

EXAMPLE

The following synthesis examples, examples of the invention and comparative examples are provided to illustrate the invention and do not in any way limit the invention.

Synthesis Example 1

Synthesis of Compound (6)

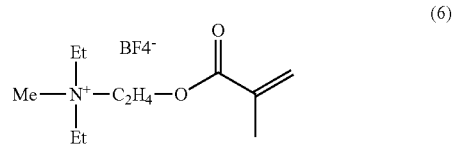

A solution was prepared by dissolving 11.7 g of diethylaminoethyl methacrylate (Wako Pure Chemical Industries, Ltd.) in 250 mL of tetrahydrofuran (Wako Pure Chemical Industries), then stirred with a stirrer under ice cooling while slowing adding a little at a time 4.71 mL of methyl iodide (Katayama Industries Co., Ltd.). After 30 minutes, the ice bath was removed and stirring was carried out overnight at room temperature. The solvent in this reaction solution was driven off by vacuum distillation, and the resulting solids were recrystallized from an ethanol (Wako Pure Chemical Industries)—tetrahydrofuran system, giving 18.17 g of the iodide salt of diethylmethylaminoethyl methacrylate.

Next, 10.80 g of silver tetrafluoroborate (Tokyo Kasei Kogyo Co., Ltd.) was dissolved in 300 mL of chloroform (Wako Pure Chemical Industries) under ice cooling, then stirred with a stirrer while slowly adding a little at a time a solution of the 18.17 g of the iodide salt of diethylmethylaminoethyl methacrylate dissolved in 50 mL of chloroform. After 30 minutes of stirring, the solvent in the reaction solution was separated off by vacuum filtration. The solvent was driven off from the resulting filtrate using an evaporator and a vacuum pump, yielding 13.01 g of the tetrafluoroborate salt of diethylmethylaminoethyl methacrylate.

Synthesis Example 2

Synthesis of Compound (7)

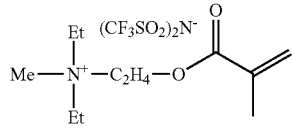

(7)

A solution was prepared by dissolving 11.7 g of diethylaminoethyl methacrylate (Wako Pure Chemical Industries, Ltd.) in 250 mL of tetrahydrofuran (Wako Pure Chemical Industries), then stirred with a stirrer under ice cooling while slowing adding a little at a time 4.71 mL of methyl iodide (Katayama Chemical Industries Co., Ltd.). After 30 minutes, the ice bath was removed and stirring was carried out overnight at room temperature. The solvent in this reaction solution was driven off by vacuum distillation, and the resulting solids were recrystallized from an ethanol (Wako Pure Chemical Industries)—tetrahydrofuran system, giving 18.17 g of the iodide salt of diethylmethylaminoethyl methacrylate.

The 18.17 g of the iodide salt of diethylmethylaminoethyl methacrylate was dissolved in 50 mL of acetonitrile (Kanto Chemical Co., Inc.), following which 15.93 g of lithium bis(trifluoromethanesulfonyl)imide (produced by Kishida Chemical Co., Ltd.) was added and completely dissolved therein, and the resulting solution was stirred for 30 minutes. The acetonitrile was removed by vacuum distillation and a suitable amount of ion-exchanged water was added to the residue. The organic phase that divided in two was subsequently separated off. Washing was similarly carried out five times with ion-exchanged water to remove impurities from the organic phase. Moisture was then removed from the washed organic phase using a vacuum pump, yielding 20.71 g of the bis(trifluorosulfonyl)imide salt of diethylmethylaminoethyl methacrylate.

Synthesis Example 3

Synthesis of Compound (10)

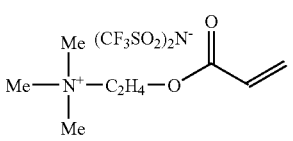

(10)

A solution was prepared by dissolving 10.0 g of N,N-dimethylaminoethyl acrylate methyl chloride (Kohjin Co., Ltd.), prepared as a 79 wt % aqueous solution, in 50 mL of ion-exchanged water. Next, 11.72 g of lithium bis(trifluoromethanesulfonyl)imide (produced by Kishida Chemical Co., Ltd.) was added and the mixture was stirred for 60 minutes. The organic phase that divided in two was subsequently separately off. A suitable amount of ion-exchanged water was similarly added and impurities within the organic phase were removed. Moisture was then removed from the washed organic phase using a vacuum pump, yielding 16.27 g of the bis(trifluorosulfonyl)imide salt of trimethylaminoethyl acrylate.

Synthesis Example 4

Synthesis of Compound (12)

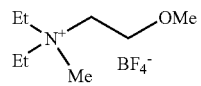

(12)

A solution prepared by mixing together 100 mL of diethylamine and 85 mL of 2-methoxyethyl chloride (both available from Kanto Chemical) was placed in an autoclave and reacted at 120° C. for 12 hours. The internal pressure during the reaction was 0.28 MPa (2.9 kgf/cm$^2$). This yielded a mixture of deposited crystals and reaction solution to which was added, following the 12 hours of reaction, 200 mL of an aqueous solution prepared by dissolving 40 g of sodium hydroxide (Katayama Chemical Industries Co., Ltd.) in 200 mL of water. Each of the two divided organic phases that formed as a result was separated off with a separatory funnel and subjected twice to extraction with 250 mL of tetrahydrofuran (Wako Pure Chemical Industries, Ltd.). The separated organic phases were then combined and washed with a saturated saline solution, following which potassium carbonate (Wako Pure Chemical Industries) was added to remove water and vacuum filtration was carried out. The solvent in the resulting organic phase was distilled off in a rotary evaporator, after which the residue was subjected to normal-pressure distillation, yielding 21 g of 2-methoxyethyldiethylamine.

Next, 8.2 g of the 2-methoxyethyldiethylamine was dissolved in 10 mL of tetrahydrofuran (Wako Pure Chemical Industries), then 4.0 mL of methyl iodide (Wako Pure Chemical Industries) was added under ice cooling. After 30 minutes, the mixture was removed from the ice bath and stirred overnight at room temperature. The solvent in this reaction solution was subsequently driven off by vacuum distillation, and the resulting solids were recrystallized from an ethanol (Wako Pure Chemical Industries)—tetrahydrofuran system, yielding 16 g of 2-methoxyethyldiethylmethylammonium iodide.

Next, 15.0 g of 2-methoxyethyldiethylmethylammonium iodide and 1.07 g of silver tetrafluoroborate (Tokyo Kasei Kogyo) were mixed, yielding 11.5 g of compound (12) which was liquid at room temperature (25° C.).

Synthesis Example 5

Synthesis of Compound (16)

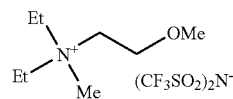

(16)

A solution was prepared by dissolving 10.0 g of 2-methoxyethyldiethylmethylammonium iodide in 50 mL of acetonitrile (Kanto Chemical). Next, 9.5 g of lithium bis(trifluoromethanesulfonyl)imide (Kishida Chemical) was added and completely dissolved therein, and the resulting solution was stirred for 15 minutes.

The acetonitrile was then removed by vacuum distillation and a suitable amount of water was added to the residue. The organic phase that divided in two was subsequently separated off. Washing was similarly carried out five times with water to remove impurities.

The washed organic phase was then placed under a reduced pressure using a vacuum pump and the water was thoroughly driven off, yielding 6.8 g of compound (16) which was liquid at room temperature (25° C.).

Synthesis Example 6

Synthesis of Imidazolium-Based Ionic Liquid

First, 5.74 g of lithium bis(trifluoromethane-sulfonyl) imide (Kishida Chemical) was added to 30 mL of a 1:1 (by volume) mixed solvent composed of chloroform and acetonitrile, and the mixture was stirred to form a suspension. Next, a solution prepared by dissolving 2.92 g of 1-ethyl-3-methylimidazolium chloride (Tokyo Kasei Kogyo) in 30 mL of a 1:1 (by volume) mixed solvent of chloroform and acetonitrile was added to the suspension, and the mixture was stirred for 80 minutes. The crystals that formed were removed by vacuum filtration, and the solvent within the filtrate was driven off with an evaporator and a vacuum pump.

Next, 4.85 g of the resulting residue was further purified by silica gel column chromatography (Wakogel C-200, produced by Wako Pure Chemical Industries; eluate, 1:1 (by volume) mixed solvent of chloroform and methanol), yielding 3.06 g of an imidazolium-based ionic liquid which was liquid at room temperature.

Synthesis Example 7

Synthesis of Polyvinyl Alcohol Derivative

A reaction vessel equipped with a stirring element was charged with 3 parts by weight of polyvinyl alcohol (average degree of polymerization, 500; vinyl alcohol fraction, ≧98%), 20 parts by weight of 1,4-dioxane and 14 parts by weight of acrylonitrile. A solution of 0.16 part by weight of sodium hydroxide in 1 part by weight of water was gradually added under stirring, after which stirring was continued for 10 hours at 25° C.

The resulting mixture was neutralized using an ion-exchange resin (produced by Organo Corporation under the trade name Amberlite IRC-76). The ion-exchange resin was then separated off by filtration, after which 50 parts by weight of acetone was added to the solution—and the insolubles were filtered off. The resulting acetone solution was placed in dialysis membrane tubing and dialyzed with running water. The polymer which precipitated within the dialysis membrane tubing was collected and re-dissolved in acetone. The resulting solution was filtered, following which the acetone was evaporated off, giving a cyanoethylated polyvinyl alcohol polymer derivative.

The infrared absorption spectrum of the resulting derivative showed no hydroxyl group absorption, confirming that all the hydroxyl groups were capped with cyanoethyl groups (capping ratio, 100%).

Synthesis Example 8

Synthesis of Thermoplastic Polyurethane Resin (Binder Polymer)

A reactor equipped with a stirrer, a thermometer and a condensing tube was charged with 60.20 parts by weight of preheated and dehydrated polyethylene glycol 4000 (PEG 4000-S, available from Sanyo Chemical Industries, Ltd.) and 7.84 parts by weight of 4,4'-diphenylmethane diisocyanate. The reactor contents were stirred and mixed for 2 hours at 120° C. under a stream of nitrogen, following which 1.86 parts by weight of 1,4-butanediol was added to the mixture and the reaction was similarly effected at 120° C. under a stream of nitrogen. When the reaction reached the point where the reaction product became rubbery, it was stopped. The reaction product was then removed from the reactor and heated at 100° C. for 12 hours. Once the isocyanate peak was confirmed to have disappeared from the infrared absorption spectrum, heating was stopped, yielding a solid polyurethane resin.

The resulting polyurethane resin had a weight-average molecular weight (Mw) of $1.05 \times 10^5$. A polyurethane resin solution was prepared by dissolving 8 parts by weight of this polyurethane resin in 92 parts by weight of N-methyl-2-pyrrolidone.

[1] Preparation of Polymer Electrolyte-Forming Compositions and Polymer Electrolytes Example 1

Thirty parts by weight of compound (6) obtained in Synthesis Example 1 as a quaternary ammonium salt (A) was mixed and dissolved in 70 parts by weight of compound (12) obtained in Synthesis Example 4 as a ionic liquid (B). To this was added 1 part by weight of a methacrylate monomer mixture (as a reactive double bond-bearing compound (C)) composed of 100 parts by weight of polyethylene glycol dimethacrylate (number of oxirene units, 9), 70.15 parts by weight of methoxypolyethylene glycol monomethacrylate (number of oxirene units, 2) and 8.41 parts by weight of trimethylolpropane trimethacrylate. Next, 0.5 part by weight of 2,2'-azobis-2,4-dimethylvaleronitrile was added, thereby giving a polymer electrolyte-forming composition. The resulting polymer electrolyte-forming composition was poured into a bottle of a fixed size and heated at 55° C. for 4 hours to effect a reaction, giving a polymer electrolyte. The cured state and physical properties of the polymer electrolyte were checked visually and by touch. The results are shown in Table 1.

Example 2

Aside from using compound (7) obtained in Synthesis Example 2 and compound (16) obtained in Synthesis Example 5 as the quaternary ammonium salt (A) and the ionic liquid (B), respectively, a polymer electrolyte-forming composition and a polymer electrolyte were obtained in the same way as in Example 1. The cured state and physical properties of the polymer electrolyte were checked visually and by touch. The results are shown in Table 1.

Example 3

Aside from using compound (16) obtained in Synthesis Example 5 as the ionic liquid (B), a polymer electrolyte-forming composition and a polymer electrolyte were obtained in the same way as in Example 1. The cured state and physical properties of the polymer electrolyte were checked visually and by touch. The results are shown in Table 1.

Example 4

Aside from using the imidazolium-based ionic liquid obtained in Synthesis Example 6 as the ionic liquid, a polymer electrolyte-forming composition and a polymer electrolyte were obtained in the same way as in Example 1. The cured state and physical properties of the polymer electrolyte were checked visually and by touch. The results are shown in Table 1.

Example 5

Aside from not adding the methacrylate monomer mixture, a polymer electrolyte-forming composition and a polymer electrolyte were obtained in the same way as in Example 1. The cured state and physical properties of the polymer electrolyte were checked visually and by touch. The results are shown in Table 1.

Example 6

Thirty parts by weight of compound (6) obtained in Synthesis Example 1 was mixed and dissolved in 70 parts by weight of compound (12) obtained in Synthesis Example 4. To this was added 1 part by weight of the methacrylate monomer mixture used in Example 1 and 0.2 part by weight of the polyvinyl alcohol derivative obtained in Synthesis Example 7 as a linear polymeric compound (E). Following stirring and dissolution, 0.5 part by weight of 2,2'-azobis-2,4-dimethylvaleronitrile was added, giving a polymer electrolyte-forming composition. A polymer electrolyte was prepared from the composition in the same way as in Example 1. The cured state and physical properties of the polymer electrolyte were checked visually and by touch. The results are shown in Table 1.

Example 7

A polymer electrolyte-forming composition was prepared by adding 20 parts by weight of NK Oligo UA-W2 (made by Shin-Nakamura Chemical Co., Ltd.) and 0.5 part by weight of 2,2'-azobis-2,4-dimethylvaleronitrile to 80 parts by weight of compound (7) obtained in Synthesis Example 2 as a quaternary ammonium salt (A').

The resulting polymer electrolyte-forming composition was poured into a bottle of a fixed size and heated at 55° C. for 0.5 hour to effect reaction, giving a polymer electrolyte. The cured state and physical properties of the polymer electrolyte were checked visually and by touch. The results are shown in Table 1.

Example 8

A polymer electrolyte-forming composition was prepared by adding 0.5 part by weight of 2,2'-dimethoxyphenylacetone to 100 parts by weight of compound (7) obtained in Synthesis Example 2 as a quaternary ammonium salt (A').

The resulting polymer electrolyte-forming composition was coated to a thickness of 0.42 mm on a quartz plate of a fixed size and irradiated with ultraviolet light for 6 seconds, thereby forming a polymer electrolyte film. The cured state and physical properties of the polymer electrolyte film were checked visually and by touch. The results are shown in Table 1.

Example 9

A polymer electrolyte-forming composition was prepared by adding 20 parts by weight of NK Oligo UA-W2 (Shin-Nakamura Chemical) and 0.5 part by weight of 2,2'-dimethoxyphenylacetone to 80 parts by weight of compound (7) obtained in Synthesis Example 2 as a quaternary ammonium salt (A').

The resulting polymer electrolyte-forming composition was coated to a thickness of 0.42 mm on a quartz plate of a fixed size and irradiated with ultraviolet light for 6 seconds, thereby forming a polymer electrolyte film. The cured state and physical properties of the polymer electrolyte film were checked visually and by touch. The results are shown in Table 1.

Example 10

A solid polymer electrolyte-forming composition was prepared by adding 20 parts by weight of the water-soluble urethane acrylate UA-W2 (Shin-Nakamura Chemical) and 0.5 part by weight of 2,2'-azobis-2,4-dimethylvaleronitrile to 80 parts by weight of compound (10) obtained in Synthesis Example 3. The resulting polymer electrolyte-forming composition was poured into a bottle of a fixed size and heated at 55° C. for 0.5 hour to effect reaction, giving a solid polymer electrolyte. The cured state and physical properties of the solid polymer electrolyte were checked visually and by touch. The results are shown in Table 1.

Example 11

A solid polymer electrolyte-forming composition was prepared by adding 0.5 part by weight of 2,2'-dimethoxyphenylacetone to 100 parts by weight of compound (10) obtained in Synthesis Example 3. The resulting polymer electrolyte-forming composition was coated to a thickness of 0.42 mm on a quartz plate of a fixed size and irradiated with ultraviolet light for 6 seconds, thereby forming a solid polymer electrolyte film. The cured state and physical properties of the solid polymer electrolyte film were checked visually and by touch. The results are shown in Table 1.

Example 12

A solid polymer electrolyte-forming composition was prepared by adding 20 parts by weight of the water-soluble urethane acrylate UA-W2 (Shin-Nakamura Chemical) and 0.5 part by weight of 2,2'-dimethoxyphenylacetone to 80 parts by weight of compound (10) obtained in Synthesis Example 3. The resulting polymer electrolyte-forming composition was coated to a thickness of 0.42 mm on a quartz plate of a fixed size and irradiated with ultraviolet light for 6 seconds, thereby forming a solid polymer electrolyte film. The cured state and physical properties of the solid polymer electrolyte film were checked visually and by touch. The results are shown in Table 1.

Comparative Example 1

Aside from not using a quaternary ammonium salt (A) and changing the amount in which the compound (12) obtained in Synthesis Example 4 was used as the ionic liquid (B) to 100 parts by weight, a polymer electrolyte-forming composition and a polymer electrolyte were obtained in the same way as in Example 1. The cured state and physical properties of the polymer electrolyte were checked visually and by touch. The results are shown in Table 1.

Comparative Example 2

Aside from using a solution prepared by dissolving tetraethylammonium tetrafluoroborate in propylene carbonate (both available from Kishida Chemical) to a concentration of 1.0 M instead of an ionic liquid, a polymer electrolyte-forming composition and a polymer electrolyte were obtained in the same way as in Example 1. The cured state and physical properties of the polymer electrolyte were checked visually and by touch. The results are shown in Table 1.

Measurements of ionic conductivity were carried out by the method described above on the polymer electrolyte-forming compositions obtained in the respective examples and comparative examples above. The results are shown in Table 1. The results obtained from the measurement of ionic conductivity using only compound (12) obtained in Synthesis Example 4 are also shown in Table 1 as a reference example.

<Measurement of Ionic Conductivity>

Test cells were fabricated as follows in Examples 1 to 7 and 10. In each case 12 sheets of cellulose separator (TF 40-35, available from Nippon Kodoshi Corporation; thickness, 0.035 mm) cut to a size of 50×20 mm were stacked and placed between two aluminum sheets cut to a size of 50×20 mm and having aluminum terminal leads attached thereto (sheet thickness, 0.02 mm; available from Nippon Foil Manufacturing Co., Ltd.). The resulting assembly was inserted into an aluminum laminate pack glued into the shape of a pouch, a polymer electrolyte-forming composition (or, in the reference example, an ionic liquid) was poured in and impregnated under a vacuum of 60 Torr for 30 minutes. Excess liquid was squeezed out, following which the pack was sealed tight with a vacuum sealer. This was followed by 4 hours of heating at 55° C. to solidify the composition, thereby giving a test cell.

In Examples 8, 9, 11 and 12, test cells were fabricated as follows. In each case, the prepared polymer electrolyte-forming composition was coated to a thickness of 0.42 mm onto an aluminum sheet having an aluminum terminal lead attached thereto, then irradiated with ultraviolet light for a specific length of time in a UV irradiator to form a polymer electrolyte film. This aluminum sheet and the polymer electrolyte film on the aluminum sheet were both cut to a size of 50×20 mm, following which an aluminum sheet cut to a size of 50×20 mm and having an aluminum terminal lead attached thereto was placed on top of the polymer electrolyte film, thereby giving a test cell.

The ionic conductivity at 25° C. of each of the test cells thus obtained was measured by the AC impedance method. In the reference example, the heating step was omitted.

TABLE 1

| | Degree of cure | Properties; Color | Ionic conductivity ($\delta$, S/cm) |
|---|---|---|---|
| Example 1 | good | flexible; clear and colorless | $7724 \times 10^{-3}$ |
| Example 2 | good | flexible; clear and colorless | $6.217 \times 10^{-3}$ |
| Example 3 | good | flexible; clear and colorless | $5.218 \times 10^{-3}$ |

TABLE 1-continued

| | Degree of cure | Properties; Color | Ionic conductivity ($\delta$, S/cm) |
|---|---|---|---|
| Example 4 | good | flexible; milky white | $4.377 \times 10^{-3}$ |
| Example 5 | fair | somewhat brittle; clear and colorless | $5.641 \times 10^{-3}$ |
| Example 6 | excellent | very strong; clear and colorless | $5.631 \times 10^{-3}$ |
| Example 7 | excellent | very strong; clear and colorless | $1.023 \times 10^{-3}$ |
| Example 8 | excellent | very strong; clear and colorless | $1.134 \times 10^{-3}$ |
| Example 9 | excellent | very strong; clear and colorless | $1.186 \times 10^{-3}$ |
| Example 10 | excellent | very strong; clear and colorless | $1.312 \times 10^{-3}$ |
| Example 11 | excellent | very strong; clear and colorless | $1.904 \times 10^{-3}$ |
| Example 12 | excellent | very strong; clear and colorless | $1.512 \times 10^{-3}$ |
| Comparative Example 1 | poor | phase separation | — |
| Comparative Example 2 | good | some flexibility; clear and colorless | $8.296 \times 10^{-4}$ |
| Reference Example | — | — | $7.342 \times 10^{-3}$ |

[2] Fabrication of Electrical Double-Layer Capacitors

Example 13

<Fabrication of Polarizable Electrodes>

Eighty-five parts by weight of activated carbon (MSP15, produced by Kansai Coke and Chemicals Co., Ltd.), 10 parts by weight of acetylene black, 50 parts by weight of a solution of 5 parts by weight of polyvinylidene fluoride dissolved in 45 parts by weight of N-methyl-2-pyrrolidone, and 165 parts by weight of N-methyl-2-pyrrolidone were stirred and mixed to give a paste-like activated carbon electrode composition. The electrode composition was coated onto aluminum oxide foil with a doctor blade to a film thickness when dry of 200 µm, then dried at 80° C. for 2 hours to form polarizable electrodes.

<Fabrication of Electrical Double-Layer Capacitor>

A stacked electrode assembly was produced by attaching aluminum terminal leads to the electrode current collectors fabricated as described above, then stacking these two electrodes opposite each other with a polyolefin nonwoven fabric separator sandwiched therebetween. Next, the electrode assembly was placed in an aluminum laminate case with the terminals emerging from the case, following which the case was filled with the polymer electrolyte-forming composition obtained in Example 1 and sealed. This was followed by 4 hours of heating at 55° C. to react the composition, thereby giving a laminate-type electrical double-layer capacitor. The resulting capacitor was found to be free of fluid leakage.

Example 14

Aside from using the polymer electrolyte-forming composition obtained in Example 2, an electrical double-layer capacitor was fabricated in the same way as in Example 13. The resulting capacitor was found to be free of fluid leakage.

Example 15

Aside from using the polymer electrolyte-forming composition obtained in Example 3, an electrical double-layer capacitor was fabricated in the same way as in Example 13. The resulting capacitor was found to be free of fluid leakage.

Example 16

Aside from using the polymer electrolyte-forming composition obtained in Example 4, an electrical double-layer capacitor was fabricated in the same way as in Example 13. The resulting capacitor was found to be free of fluid leakage.

Example 17

Aside from using the polymer electrolyte-forming composition obtained in Example 5, an electrical double-layer capacitor was fabricated in the same way as in Example 13. The resulting capacitor was found to be free of fluid leakage.

Example 18

Aside from using the polymer electrolyte-forming composition obtained in Example 6, an electrical double-layer capacitor was fabricated in the same way as in Example 13. The resulting capacitor was found to be free of fluid leakage.

Example 19

Aside from using the polymer electrolyte-forming composition obtained in Example 7, an electrical double-layer capacitor was fabricated in the same way as in Example 13. The resulting capacitor was found to be free of fluid leakage.

Example 20

Aside from using the polymer electrolyte-forming composition obtained in Example 10, an electrical double-layer capacitor was fabricated in the same way as in Example 13. The resulting capacitor was found to be free of fluid leakage.

Comparative Example 3

Aside from using only compound (12) obtained in Synthesis Example 4 as the electrolyte, an electrical double-layer capacitor was fabricated in the same way as in Example 13. Fluid leakage was found to occur in the resulting capacitor.

The electrostatic capacitances of the electrical double-layer capacitors obtained in Examples 13 to 20 and in Comparative Example 3 were determined by carrying out charge-discharge tests using a charge-discharge unit under the conditions indicated below. The results are shown in Table 2.

<Electrostatic Capacitance>

Constant-current charge and discharge were carried out at a cut-off voltage during charging of 2.5 V, an end of discharge voltage of 0 V, and a current density of 1.5 mA/cm$^2$. The electrostatic capacitance was computed from the integrated value for the electrical energy at the time of discharge.

TABLE 2

|  | Liquid leakage | Electrostatic capacitance (F/g) |
|---|---|---|
| Example 13 | no | 32.1 |
| Example 14 | no | 31.7 |
| Example 15 | no | 30.6 |
| Example 16 | no | 27.0 |
| Example 17 | no | 31.8 |
| Example 18 | no | 31.4 |
| Example 19 | no | 20.8 |
| Example 20 | no | 22.1 |
| Comparative Example 3 | yes | 32.0 |

As is apparent from Table 2, unlike the electrical double-layer capacitor in Comparative Example 3, the polymer electrolyte-containing electrical double-layer capacitors obtained in Examples 13 to 20 were found to be free of fluid leakage and had excellent safety. Moreover, the differences among the electrostatic capacitances for the electrical double-layer capacitors in Examples 13 to 20 demonstrate that, as the structures of the quaternary ammonium salt (A) and the ionic liquid (B) become more similar and ultimately identical, a more uniform gel or film is obtained, the electrical conductivity becomes higher, and the capacitor characteristics become even better.

[3] Fabrication of Lithium Polymer Secondary Cells

Example 21

<Fabrication of Positive Electrode>

A paste-like positive electrode binder composition was prepared by stirring and mixing together 90 parts by weight of LiCoO$_2$ as the positive electrode active material, 6 parts by weight of Ketjenblack as the conductive material, 40 parts by weight of a solution of 10 parts by weight of polyvinylidene fluoride (PVdF) in 90 parts by weight of N-methyl-2-pyrrolidone, and 20 parts by weight of N-methyl-2-pyrrolidone. The positive electrode binder composition was applied onto aluminum foil with a doctor blade to a film thickness when dry of 100 μm. This was followed by 2 hours of drying at 80° C., thereby giving a positive electrode.

<Fabrication of Negative Electrode>

A paste-like negative electrode binder composition was prepared by stirring and mixing together 90 parts by weight of mesophasecarbon microbeads (MCMB 6-28, made by Osaka Gas Chemicals Co., Ltd.) as the negative electrode active material, 100 parts by weight of a solution of 10 parts by weight of polyvinylidene fluoride (PVdF) in 90 parts by weight of N-methyl-2-pyrrolidone, and 20 parts by weight of N-methyl-2-pyrrolidone. The negative electrode binder composition was applied onto copper foil with a doctor blade to a film thickness when dry of 100 μm. This was followed by 2 hours of drying at 80° C., thereby giving a negative electrode.

<Fabrication of Secondary Cell>

The positive electrode was cut such as to make the size of the coated area 5×48 cm, and the negative electrode was cut such as to make the size of the coated area 5.2×28.2 cm. The separator base was sandwiched between these cut positive and negative electrodes, and the resulting stack was placed in an aluminum laminate case, giving a cell assembly. The polymer electrolyte-forming composition obtained in Example 1 was introduced into this electrode assembly and the laminate was sealed. The cell assembly was heated at 55° C. for four hours to effect reactive curing, thereby giving a laminate-type lithium polymer secondary cell. The secondary cell was found to be free of fluid leakage.

Examples 22 to 28

Aside from using the polymer electrolyte-forming compositions obtained in Examples 2 to 7 and in Example 10, lithium secondary cells were fabricated in the same way as in Example 21. The resulting lithium secondary cells were found to be free of fluid leakage.

Comparative Example 4

Aside from using only compound (12) obtained in Synthesis Example 4 as the electrolyte, a lithium secondary cell was fabricated in the same way as in Example 21. Fluid leakage was found to occur in the resulting lithium secondary cell.

The capacities of the lithium cells obtained in Examples 21 to 28 and in Comparative Example 4 were determined by carrying out charge-discharge tests using a charge-discharge unit under the conditions indicated below. The results are shown in Table 3.

<Charge-Discharge Test>

Constant-current charge and discharge were carried out at a cut-off voltage during charging of 4.2 V, an end of discharge voltage of 2.7 and a current density of 0.5 mA/cm$^2$, and the cell capacity (mAh) was measured.

TABLE 3

|  | Liquid leakage | Capacity (mAh) |
| --- | --- | --- |
| Example 21 | no | 610.8 |
| Example 22 | no | 602.3 |
| Example 23 | no | 597.6 |
| Example 24 | no | 598.3 |
| Example 25 | no | 608.2 |
| Example 26 | no | 602.5 |
| Example 27 | no | 592.5 |
| Example 28 | no | 591.7 |
| Comparative Example 4 | yes | 612.0 |

As is apparent from Table 3, unlike the lithium secondary cell in Comparative Example 4, the polymer electrolyte-containing lithium secondary cells obtained in Examples 21 to 28 were found to be free of fluid leakage and had excellent safety. Moreover, the differences among the capacities for the lithium secondary cells in Examples 21 to 28 demonstrate that, as the structures of the quaternary ammonium salt (A) and the ionic liquid (B) become more similar and ultimately identical, a more uniform gel or film is obtained, the electrical conductivity becomes higher, and the cell characteristics become even better.

The invention claimed is:

1. A polymer electrolyte-forming composition characterized by comprising:
    (A) a quaternary arnmoniuin salt of general formula (1) below

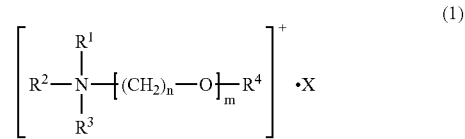

wherein R$^1$ to R$^3$ are each independently an alkyl group of 1 to 5 carbons or a substituent having a reactive unsaturated bond and any two from among R$^1$ to R$^3$ may together form a ring, R$^4$ is methyl, ethyl or a substituent having a reactive unsaturated bond, with the proviso that at least one of R$^1$ to R$^4$ is a substituent having a reactive unsaturated bond, X is a monovalent anion, the letter m is an integer from 1 to 8, and the letter n is an integer from 1 to 4; and
    (B) an ionic liquid that is a quaternary ammonium salt of general formula (2) below

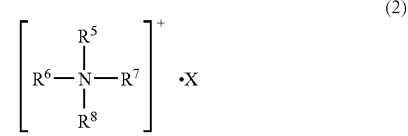

wherein R$^5$ to R$^8$ are each independently an alkyl of 1 to 5 carbons or an alkoxyalkyl group of the formula R'—O—(CH$_2$)$_n$— (R' being methyl or ethyl, and the letter n being an integer from 1 to 4) and any two from among R$^5$, R$^6$, R$^7$ and R$^8$ may together form a ring, with the proviso that at least one of R$^5$ to R$^8$ is an alkoxyalkyl group of the above formula, and X is a monovalent anion.

2. The polymer electrolyte-forming composition of claim 1, wherein X is at least one selected from among BF$_4^-$, PF$_6^-$, (CF$_3$SO$_2$)$_2$N$^-$, CF$_3$SO$_3^-$ and CF$_3$CO$_2^-$.

3. The polymer electrolyte-forming composition of claim 1, further comprising (C) a reactive double bond-bearing compound.

4. The polymer electrolyte-forming composition of claim 1, further comprising (D) an ion-conductive salt.

5. The polymer electrolyte-forming composition of claim 1, further comprising (E) a straight-chain or branched linear polymeric compound.

6. A polymer electrolyte which is characterized in that it can be obtained by reacting the polymer electrolyte-forming composition according to claim 1.

7. A polymer electrolyte-forming composition characterized by comprising:
    (A) a quaternary ammonium salt of general formula (1) below

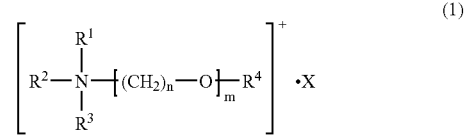

wherein R$^1$ to R$^3$ to are each independently an alkyl group of 1 to 5 carbons or a substituent having a reactive unsaturatud bond and any two from among R$^1$ to R$^3$ may together form a ring, $R^4$ is methyl, ethyl or a substituent having a reactive unsaturated bond, with the proviso that at least one of $R^1$ to $R^4$ is a substituent having a reactive unsaturated bond, X is a monovalent anion, the letter m is an integer from 1 to 8, and the letter n is an integer from 1 to 4; and (B) an ionic liquid;

wherein the quaternary animonium salt (A) and/or the ionic liquid (B) has a partial structure of formula (3) below $$\text{H}_3\text{C}-\underset{\underset{\text{C}_2\text{H}_5}{|}}{\overset{\overset{\text{C}_2\text{H}_5}{|}}{\text{N}^+}}-(\text{C}_2\text{H}_4-\text{O})_{\overline{m}} \quad (3)$$

wherein the letter m is an integer from 1 to 8.

8. The poiymer electrolyte-forming composition of claim 7, wherein X is at least one selected from among $BF_4^-$, $PF_6^-$, $(CF_3SO_2)_2N^-$, $CF_3SO_3^-$ and $CF_3CO_2^-$.

9. The polymer electrolyte-forming composition of claim 7, further comprising (C) a reactive double bond-bearing compound.

10. The polymer electrolyte-forming composition of claim 7, further comprising (D) an ion-conductive salt.

11. The polymer electrolyte-forming composition of claim 7, further comprising (E) a straight-chain or branched linear polymeric compound.

12. A polymer electrolyte which is characterized in that it can be obtained by reacting the polymer electrolyte-forming composition according to claim 7.

13. A polymer electrolyte-forming composition characterized by comprising:

(A') a quaternary ammonium salt which has general formula (1) below and has the properties of an ionic liquid $$\left[ R^2-\underset{\underset{R^3}{|}}{\overset{\overset{R^1}{|}}{\text{N}}}-[(\text{CH}_2)_n-\text{O}]_m-R^4 \right]^+ \cdot X \quad (1)$$

wherein $R^1$ to $R^3$ are each independently an alkyl group of 1 to 5 carbons or a substituent having a reactive unsaturated bond and any two from among $R^1$ to $R^3$ may together form a ring, $R^4$ is methyl, ethyl or a substituent having a reactive unsaturated bond, with the proviso that at least one of $R^1$ to $R^4$ is a substituent having a reactive unsaturated bond, X is a monovalent anion, the letter m is an integer from 1 to 8, and the letter n is an integer from 1 to 4, and (A') has a partial structure of formula (3) below $$\text{H}_3\text{C}-\underset{\underset{\text{C}_2\text{H}_5}{|}}{\overset{\overset{\text{C}_2\text{H}_5}{|}}{\text{N}^+}}-(\text{C}_2\text{H}_4-\text{O})_{\overline{m}} \quad (3)$$

wherein the letter m is an integer from 1 to 8.

14. An electrical double-layer capacitor comprising a pair of polarizable electrodes, a separator between the polarizable electrodes, and an electrolyte;

which electrical double-layer capacitor is characterized in that the electrolyte is a polymer electrolyte obtained by reacting a polymer electrolyte-forming composition, wherein the polymer electrolyte-forming composition-comprises:

(A) a quatemary ammonium salt of general formula (1) below $$\left[ R^2-\underset{\underset{R^3}{|}}{\overset{\overset{R^1}{|}}{\text{N}}}-[(\text{CH}_2)_n-\text{O}]_m-R^4 \right]^+ \cdot X \quad (1)$$

wherein $R^1$ to $R^3$ are each independently an alkyl group of 1 to 5 carbons or a substituent having a reactive unsaturated bond and any two from among $R^1$ to $R^3$ may together form a ring, $R^4$ is methyl, ethyl or a substituent having a reactive unsaturated bond, with the proviso that at least one of $R^1$ to $R^4$ is a substituent having a reactive unsaturated bond, X is a monovalent anion, the letter m is an integer from 1 to 8, and the letter n is an integer from 1 to 4; and (B) an ionic liquid.

15. A nonaqueous electrolyte secondary cell comprising a positive electrode which contains a lithium-containing compound oxide, a negative electrode which contains a carbonaceous material capable of lithium ion insertion and extraction or contains metallic lithium, a separator between the positive and negative electrodes, and-an electrolyte;

which nonaqueous electrolyte secondary cell is characterized in that the electrolyte is a polymer electrolyte obtained by reacting a polymer electrolyte-fonning composition, whereinthe polymer electrolyte-forming composition comprises:

(A) a quaternary animonium salt of general formula (1) below $$\left[ R^2-\underset{\underset{R^3}{|}}{\overset{\overset{R^1}{|}}{\text{N}}}-[(\text{CH}_2)_n-\text{O}]_m-R^4 \right]^+ \cdot X \quad (1)$$

wherein $R^1$ to $R^3$ are each independently an alkyl group of 1 to 5 carbons or a substituent having a reactive unsaturated bond and any two from among $R^1$ to $R^3$ may together form a ring, $R^4$ is methyl, ethyl or a substituent having a reactive unsaturated bond, with the proviso that at least one of $R^1$ to $R^4$ is a substituent having a reactive unsaturated bond, X is a monovalent anion, the letter m is an integer from 1 to 8, and the letter n is an integer from 1 to 4; and (B) an ionic liquid.

* * * * *